United States Patent
Lu

(10) Patent No.: US 11,058,131 B2
(45) Date of Patent: Jul. 13, 2021

(54) ESCHERICHIA COLI O157:H7 BACTERIOPHAGE Φ241

(71) Applicant: Kennesaw State University Research and Service Foundation, Inc., Kennesaw, GA (US)

(72) Inventor: Zhongjing Lu, Canton, GA (US)

(73) Assignee: Kennesaw State University Research and Service Foundation, Inc., Kennesaw, GA (US)

( * ) Notice: Subject to any disclaimer, the term of this patent is extended or adjusted under 35 U.S.C. 154(b) by 313 days.

(21) Appl. No.: 15/566,267

(22) PCT Filed: Apr. 15, 2016

(86) PCT No.: PCT/US2016/027695
§ 371 (c)(1),
(2) Date: Oct. 13, 2017

(87) PCT Pub. No.: WO2016/168560
PCT Pub. Date: Oct. 20, 2016

(65) Prior Publication Data
US 2018/0092386 A1 Apr. 5, 2018

Related U.S. Application Data

(63) Continuation of application No. PCT/US2016/027695, filed on Apr. 15, 2016.

(60) Provisional application No. 62/148,502, filed on Apr. 16, 2015.

(51) Int. Cl.
| | |
|---|---|
| C12Q 1/04 | (2006.01) |
| C12Q 1/70 | (2006.01) |
| C12N 7/04 | (2006.01) |
| G01N 33/569 | (2006.01) |
| A23L 3/3463 | (2006.01) |
| C12N 7/00 | (2006.01) |
| A61K 35/76 | (2015.01) |

(52) U.S. Cl.
CPC .............. *A23L 3/3463* (2013.01); *C12N 7/00* (2013.01); *C12N 7/045* (2013.01); *C12Q 1/04* (2013.01); *C12Q 1/70* (2013.01); *G01N 33/56916* (2013.01); *A61K 35/76* (2013.01); *C12N 2795/10021* (2013.01); *C12N 2795/10032* (2013.01); *Y02A 50/30* (2018.01)

(58) Field of Classification Search
CPC ......... A23L 3/3463; A61K 35/76; C12Q 1/04; C12Q 1/70; C12N 7/00; C12N 2795/10021; C12N 2795/10032; C12N 7/045; Y02A 50/30; G01N 33/56916
USPC ....................................................... 426/335
See application file for complete search history.

(56) References Cited

U.S. PATENT DOCUMENTS

| | | |
|---|---|---|
| 4,851,240 A | 7/1989 | Day et al. |
| 4,891,210 A | 1/1990 | Norris |
| 4,957,686 A | 9/1990 | Norris |
| 5,573,801 A | 11/1996 | Wilhoit |
| 5,660,812 A | 8/1997 | Merril et al. |
| 6,121,036 A | 9/2000 | Ghanbari et al. |
| 6,322,783 B1 | 11/2001 | Takahashi |
| 6,461,608 B1 | 10/2002 | Averback et al. |
| 6,485,902 B2 | 11/2002 | Waddell et al. |
| 6,544,729 B2 | 4/2003 | Sayler et al. |
| 6,699,701 B1 | 3/2004 | Sulakvelidze et al. |
| 6,896,882 B2 | 5/2005 | Ramachandran et al. |
| 7,601,347 B2 | 10/2009 | Waddell et al. |
| 7,625,556 B2 | 12/2009 | Sulakvelidze et al. |
| 7,625,741 B2 | 12/2009 | Pasternack et al. |
| 7,635,584 B2 | 12/2009 | Sulakvelidze et al. |
| 7,674,467 B2 | 3/2010 | Sulakvelidze et al. |
| 7,745,194 B2 | 6/2010 | Pasternack et al. |
| 7,807,149 B2 | 10/2010 | Soothill et al. |
| 7,951,579 B2 | 5/2011 | Hargis et al. |
| 7,985,573 B2 | 7/2011 | Yacoby et al. |
| 8,148,131 B2 | 4/2012 | Kang et al. |
| 8,241,498 B2 | 8/2012 | Summer et al. |
| 8,273,564 B2 | 9/2012 | Chen et al. |
| 8,288,146 B2 | 10/2012 | Kang et al. |
| 8,293,515 B2 | 10/2012 | Shin et al. |

(Continued)

FOREIGN PATENT DOCUMENTS

| | | |
|---|---|---|
| CN | 102181403 A | 9/2011 |
| CN | 107161425 A | 9/2017 |

(Continued)

OTHER PUBLICATIONS

Lu et al., "*Escherichia coli* O 157:H7 bacteriophage phi241 isolated from an industrial cucumber fermentation at high acidity and salinity," Front Microbiol., 6:67 (1-10), Feb. 17, 2015.

(Continued)

*Primary Examiner* — Bhaskar Mukhopadhyay
(74) *Attorney, Agent, or Firm* — Smith, Gambrell & Russell LLP

(57) ABSTRACT

Phage Φ241 specific for *Escherichia coli* O157:H7 was isolated from an industrial cucumber fermentation where both acidity (pH≤3.7) and salinity (≥5% NaCl) were high. A method for preparing a food item at least substantially free of *Escherichia coli* O157:H7 contamination contacted the food item with a bacteriophage Φ241 under conditions for the bacteriophage Φ241 to lyse all or substantially all the *Escherichia coli* O157:H7 present in the food item, while *Escherichia coli* strains other than O157:H7 were not affected. A method for detecting the presence of *Escherichia coli* O157:H7 by contacting a bacteriophage Φ241 with a food item is also disclosed.

18 Claims, 7 Drawing Sheets

(56) References Cited

U.S. PATENT DOCUMENTS

| | | | |
|---|---|---|---|
| 8,309,077 B2 | 11/2012 | Murthy et al. |
| 8,329,442 B2 | 12/2012 | Shin et al. |
| 8,475,787 B2 | 7/2013 | Harper |
| 8,591,880 B2 | 11/2013 | Chou et al. |
| 8,597,928 B2 | 12/2013 | Yang et al. |
| 9,277,763 B2 | 3/2016 | Beckman et al. |
| 9,357,785 B2 | 6/2016 | Gonzalez et al. |
| 9,358,258 B2 | 6/2016 | Kim et al. |
| 9,433,653 B2 | 9/2016 | Yoon et al. |
| 9,453,247 B2 | 9/2016 | Summer et al. |
| 9,464,267 B2 | 10/2016 | Summer et al. |
| 9,486,007 B2 | 11/2016 | Burnett et al. |
| 9,518,252 B2 | 12/2016 | Grallert et al. |
| 9,560,873 B2 | 2/2017 | Burnett et al. |
| 9,650,272 B2 | 5/2017 | Summer et al. |
| 9,657,277 B2 | 5/2017 | Shin et al. |
| 9,717,768 B2 | 8/2017 | Yang et al. |
| 9,861,102 B2 | 1/2018 | Markesbery et al. |
| 9,862,935 B2 | 1/2018 | Shin et al. |
| 9,921,219 B2 | 3/2018 | Elias et al. |
| 9,938,506 B2 | 4/2018 | Seo et al. |
| 9,950,015 B2 | 4/2018 | Cimino et al. |
| 9,950,018 B2 | 4/2018 | Shin et al. |
| 10,028,984 B2 | 7/2018 | Yoon et al. |
| 10,098,358 B2 | 10/2018 | Brown et al. |
| 10,104,903 B2 | 10/2018 | Sunvold et al. |
| 10,111,458 B1 | 10/2018 | Marshall et al. |
| 10,124,027 B2 | 11/2018 | Harper et al. |
| 10,175,176 B2 | 1/2019 | Chuang et al. |
| 10,226,060 B2 | 3/2019 | Yoon et al. |
| 10,227,570 B2 | 3/2019 | Yoon et al. |
| 10,227,571 B2 | 3/2019 | Yoon et al. |
| 10,240,129 B2 | 3/2019 | Shin et al. |
| 10,258,035 B2 | 4/2019 | Fast et al. |
| 10,265,353 B2 | 4/2019 | Yoon et al. |
| 10,265,354 B2 | 4/2019 | Yoon et al. |
| 10,265,355 B2 | 4/2019 | Yoon et al. |
| 10,265,356 B2 | 4/2019 | Yoon et al. |
| 10,357,522 B2 | 7/2019 | Regeimbal et al. |
| 10,568,917 B2 | 2/2020 | Yoon et al. |
| 10,577,590 B2 | 3/2020 | Shin et al. |
| 10,603,396 B2 | 3/2020 | Markesbery et al. |
| 10,711,252 B2 | 7/2020 | Pasternack et al. |
| 10,772,964 B2 | 9/2020 | Katsarava et al. |
| 2002/0090356 A1 | 7/2002 | Waddell et al. |
| 2004/0191224 A1 | 9/2004 | Sulakvelidze et al. |
| 2005/0175991 A1 | 8/2005 | Sulakvelidze et al. |
| 2008/0260697 A1 | 10/2008 | Murthy et al. |
| 2008/0267900 A1 | 10/2008 | Steinbrenner et al. |
| 2008/0311082 A1 | 12/2008 | Murthy et al. |
| 2009/0104157 A1 | 4/2009 | Solomon et al. |
| 2009/0155217 A1 | 6/2009 | Pasternack et al. |
| 2009/0246336 A1 | 10/2009 | Burnett et al. |
| 2011/0052541 A1 | 3/2011 | Shin et al. |
| 2011/0052543 A1 | 3/2011 | Shin et al. |
| 2011/0300528 A1 | 12/2011 | Jassim et al. |
| 2014/0030382 A1 | 1/2014 | Ter Haar et al. |
| 2014/0234391 A1 | 8/2014 | Murthy |
| 2014/0302216 A1 | 10/2014 | Stark et al. |
| 2015/0282516 A1 | 10/2015 | Heinz et al. |
| 2017/0135358 A1 | 5/2017 | Curtis-Fisk et al. |
| 2017/0156380 A1 | 6/2017 | Curtis-Fisk et al. |
| 2017/0215441 A1 | 8/2017 | Curtis-Fisk et al. |
| 2019/0321423 A1 | 10/2019 | Yoon et al. |
| 2019/0321424 A1 | 10/2019 | Yoon et al. |
| 2019/0380355 A1 | 12/2019 | Hagens et al. |
| 2020/0146315 A1 | 5/2020 | Sawyer et al. |
| 2020/0281232 A1 | 9/2020 | Clark et al. |

FOREIGN PATENT DOCUMENTS

| | | |
|---|---|---|
| CN | 105767006 B | 5/2018 |
| CN | 108179135 A | 6/2018 |
| CN | 108179136 A | 6/2018 |
| EP | 0414304 B1 | 11/1994 |
| KR | 100949389 B1 | 3/2010 |
| KR | 101023995 B1 | 3/2011 |
| KR | 101101376 B1 | 1/2012 |
| KR | 101188611 B1 | 10/2012 |
| KR | 102064765 B1 | 1/2020 |
| WO | 200975884 A1 | 6/2009 |
| WO | 2010123200 A2 | 10/2010 |
| WO | 201610751 A1 | 1/2016 |
| WO | 2016/168560 A1 | 10/2016 |
| WO | 201779715 A1 | 5/2017 |
| WO | 2019164194 A1 | 8/2019 |
| WO | 2019229079 A1 | 12/2019 |
| WO | 202013451 A1 | 1/2020 |

OTHER PUBLICATIONS

Oberst et al., "PCR-based DNA amplification and presumptive detection of *Escherichia coli* O157:H7 with an internal fluorogenic probe and the 5' nuclease (TaqMan) assay," Appl. Environ. Microbiol. 64 (3389-96), Sep. 1, 1998.

Schmelcher et al., "Application of bacteriophages for detection of foodborne pathogens," Bacteriophage, 4:e28137 (1-14), Feb. 7, 2014.

Corbitt et al., "Adenylate kinase amplification of ATP bioluminescence for hygiene monitoring in the food and beverage industry," Lett. Appl. Microbiol., 30 (443-7), Jul. 1, 2000.

International Search Report and Written Opinion issued in parent PCT/US2016/027695, dated Aug. 8, 2016.

International Preliminary Report on Patentability issued in parent PCT/US2016/027695, dated Feb. 3, 2017.

Abuladze et al. (2008). Bacteriophages reduce experimental contamination of hard surfaces, tomato, spinach, broccoli, and ground beef by *Escherichia coli* O157:H7. Appl. Environ. Microbiol. 74, 6230-6238. doi:10.1128/AEM.01465-08.

Adams (1959). Bacteriophage. New York: Interscience Publishers, Inc.

Allison and Klaenhammer (1998). Phage resistance mechanisms in lactic acid bacteria. Int. Dairy J. 8, 207-226. doi: 10.1016/S0958-6946(98)00043-0.

Anonymous. (1993). Update: multistate outbreak of *Escherichia coli* O157:H7 infections from hamburgers—Western United States, 1992-1993. Morb. Mortal. Wkly. Rep. 42, 258-263.

Anonymous. (1995). *Escherichia coli* O157:H7 outbreak linked to commercially distributed dry-cured salami. Morb. Mortal. Wkly. Rep. 44, 157-160.

Anonymous. (1996). Outbreak of *Escherichia coli* O157:H7 infections associated with drinking unpasteurized commercial apple juice—British Columbia, California, Colorado, and Washington, Oct. 1996. Morb. Mortal. Wkly. Rep. 45, 975.

Anonymous. (2006). Ongoing multistate outbreak of *Escherichia coli* serotype O157:H7 infections associated with consumption of fresh spinach—United States, Sep. 2006. Morb. Mortal. Wkly. Rep. 55, 1045-1046.

Anonymous. (2010). Investigation Update: Multistate Outbreak of *E. coli* O157:H7 Infections Associated with Cheese. Available at: http://www.cdc.gov/ecoli/2010/cheese0157/index.html [accessed Jan. 17, 2015].

Anonymous. (2011). Investigation Announcement: Multistate Outbreak of *E. coli* O157:H7 Infections Associated with Lebanon Bologna. Available at: http://www.cdc.gov/ecoli/2011/0157_0311/index.html [accessed Jan. 17, 2015].

Anonymous. (2012a). Investigation Announcement: Multistate Outbreak of *E.coli* O157:H17 Infections Linked to Romaine Lettuce. Available at: http://www.cdc.gov/ecoli/2011/ecoliO157/romainelettuce/120711/index.html [accessed Oct. 26, 2012].

Anonymous. (2012b). Multistate Outbreak of Shiga Toxin-producing *Escherichia coli* O157:H7 Infections Linked to Organic Spinach and Spring Mix Blend (Final Update). Available at: http://www.cdcgov/ecoli/2012/0157H7-11-12/index.html [accessed Jan. 17, 2015].

Anonymous. (2013). Multistate Outbreak of Shiga toxin-producing *Escherichia coli* O157:H7 Infections Linked to Ready-to-Eat Salads

(56) References Cited

OTHER PUBLICATIONS (Final Update). Available at: http://www.cdc.gov/ecoli/2013/0157H7-11-13/index.html [accessed Jan. 17, 2015].
Anonymous. (2014). Multistate Outbreak of Shiga toxin-producing *Escherichia coli* O157:H7 Infections Linked to Ground Beef (Final Update). Available at: http://www.cdc.gov/ecoli/2014/0157H7-05-14/index.html [accessed Jan. 17, 2015].
Bao and Wang (2011). Isolation and characterization of bacteriophages of *Salmonella enterica* serovar Pullorum. Poultry Sci. 90, 2370-2377. doi: 10.3382/ps.2011-01496.
Barrangou et al. (2007). CRISPR provides acquired resistance against viruses in prokaryotes. Science 315, 1709-1712. doi: 10.1126/science.1138140.
Bartual et al. (2010). Structure of the bacteriophage T4 long tail fiber receptor-binding tip. Proc. Natl. Acad. Sci. U.S.A. 107, 20287-20292. doi: 10.1073/pnas.1011218107.
Bell et al. (1994). A multistate outbreak of *Escherichia coli* O157:H7-associated bloody diarrhea and hemolytic uremic syndrome from hamburgers: the Washington experience. JAMA 272, 1349-1353. doi: 10.1001/jama.1994.03520170059036.
Berk et al. (2005). Acid resistance variability among isolates of *Salmonella entericaserovar* Typhimurium DT 104. J. Appl. Microbiol. 99, 859-866. doi: 10.1111/j.1365-2672.2005.02658.x.
Besser et al. (1993). An outbreak of diarrhea and hemolytic uremic syndrome from *Escherichia coli* O157:117 in fresh-pressed apple cider. JAMA 269, 2217-2220. doi: 10.1001/jama.1993.03500170047032.
Bickle and Kruger (1993). Biology of DNA restriction. Microbiol. Rev. 57, 434-450.
Bilge et al. (1996). Role of the *Escherichia coli* O157:H7 O side chain in adherence and analysis of an rfb locus. Infect. Immun. 64, 4795-4801.
Bokete et al. (1997). Genetic and phenotypic analysis of *Escherichia coli* with enteropathogenic characteristics isolated from Seattle children. J. Infect. Dis. 175, 1382-1389. doi: 10.1086/5164 70.
Bopp et al. (2003). Detection, isolation, and molecular subtyping of *Escherichia coli* O157:H7 and Campylobacter jejuni associated with a large waterborne outbreak. J. Clin. Microbiol. 41, 174-180. doi: 10.1128/JCM.41.1.174-180.2003.
Bosilevac and Koohmaraie (2011 ). Prevalence and characterization of non-O157 Shiga toxin-producing *Escherichia coli* isolated from commercial ground beef in the United States. Appl. Environ. Microbiol. 77, 2103-2112. doi: 10.1128/AEM.02833-10.
Breidt and Caldwell (2011). Survival of *Escherichia coli* O157:H7 in cucumber fermentation brines. J. Food Sci. 76, M198-M203. doi: 10.1111/j.1750-3841.2011.02045.x.
Breidt et al. (2013). "Fermented vegetables," in Food Microbiology: Fundamentals and Frontiers, 4th Edn, eds M. P. Doyle and L. R. Beuchat (Washington, DC: ASM Press), 841-855.
Carter et al. (2012). Bacteriophage cocktail significantly reduces *Escherichia coli* O157:H7 contamination of lettuce and beef, but does not protect against recontamination. Bacteriophage 2, 178-185. doi: 10.4161/bact.22825.
Castanie-Comet et al. (1999). Control of acid resistance in *Escherichia coli*. J. Bacterial. 181, 3525-3535.
Ceyssens et al. (2006). Genomic analysis of Pseudomonas aeruginosa phages LKD16 and LKA1: establishment of the ct>KMV subgroup within the T7 supergroup. J. Bacterial. 188, 6924-6931. doi: 10.1128/JB.00831-06.
Chang et al. (2005) Isolation and characterization of novel giant *Stenotrophomonas maltophilia* phage phiSMA5. Appl. Environ. Microbiol. 71, 1387-1393. doi: 10.1128/AEM.71.3.1387-1393.2005.
Chen and Jiang (2014) Microbiological safety of chicken litter or chicken litter-based organic fertilizers: a review. Agriculture 4, 1-29. doi: 10.3390/agriculture4010001.
Cheville et al. (1996) rpoS regulation of acid, heat, and salt tolerance in *Escherichia coli* O157:H7. Appl. Environ. Microbiol. 62, 1822-1824.

Cleary (1988) Cytotoxin producing *Escherichia coli* and the hemolytic uremic syndrome. Pediatr. Clin. N. Am. 35, 458-501.
Cody et al. (1999) An outbreak of *Escherichia coli* O157:H7 infection from unpasteurized commercial apple juice. Annu. Intern. Med. 130, 202-209. doi: 10.7326/0003-4819-130-3-199902020-00005.
Coffey et al. (2010) Phage and their lysins as biocontrol agents for food safety applications. Annu. Rev. Food Sci. Technol. 1, 449-468. doi: 10.1146/annurev.food.102308.124046.
Como-Sebetti et al. (1997) Outbreaks of *Escherichia coli* O157:H7 infection associated with eating alfalfa sprouts—Michigan and Virginia, Jun.-Jul. 1997. Morb. Mortal. Wkly. Rep. 46, 741-744.
Diez-Gonzalez and Russell (1999) Factors affecting the extreme acid resistance of *Escherichia coli* O157:H7. Food Microbiol. 16, 367-374. doi: 10.1006/fmic.1998.0249.
Ellis and Delbruck (1939) The growth of bacteriophage. J. Gen. Physiol. 22, 365-384. doi: 10.1085/jgp.22.3.365.
Farber and Pagotto (1992) The effect of acid shock on the heat resistance of Listeria monocytogenes. Lett. Appl. Microbiol. 15, 197-201. doi: 101111/j.1472-765X.1992.tb00762.x.
Ferguson et al. (2013) Lytic bacteriophages reduce *Escherichia coli* O157:H7 on fresh cut lettuce introduced through cross-contamination. Bacteriophage 3:e24323. doi: 10.4161/bact.24323.
Foschino et al. (1995) Characterization of two virulent Lactobacillus fermentum bacteriophages isolated from sour dough. J. Appl. Microbiol. 79, 677-683.
Garcia-Doval and van Raaij (2012) Structure of the receptor-binding carboxyl-terminal domain of bacteriophage T7 tail fibers. Proc. Natl. Acad. Sci. U.S.A. 109, 9390-9395. doi: 10.1073/pnas.1119719109.
Glass et al. (1992) Fate of *Escherichia coli* O157:H7 as affected by pH or sodium chloride and in fermented, dry sausage. Appl. Environ. Microbiol. 58, 2513-2516.
Griffin and Tauxe (1991) the epidemiology of infections caused by *Escherichia coli* O157:H7, other enterohemorrhagic *E. coli* and the associated hemolytic uremic syndrome. Epidemiol. Rev. 13, 60-98.
Guenther et al. (2009) Virulent bacteriophage for efficient biocontrol of Listeria monocytogenes in ready-to-eat foods. Appl. Environ. Microbiol. 75, 93-100. doi: 10.1128/AEM.01711-08.
Gyles (2007) Shiga toxin-producing *Escherichia coli*: an overview. J. Anim Sci. 85(E. Suppl.), E45-E62.
Hagens and Loessner (2010) Bacteriophage for biocontrol of food borne pathogens: calculations and considerations. Curr. Pharm. Biotechnol. 11, 58-68. doi: 10.2174/138920110790725429.
Hashemolhosseini et al. (1994) Alterations of receptor specificities of coliphages of the T2 family. J. Mo/. Biol. 240, 105-110. doi: 10.1006/jmbi.1994.1424.
Hilbom et al. (2000) an outbreak of *Escherichia coli* O157:117 infections and haemolytic uraemic syndrome associated with consumption of unpasteurized apple cider. Epidemiol. Infect. 124, 31-36. doi: 10.1017/S0950268899003258.
Hill (1993) Bacteriophage and bacteriophage resistance in lactic acid bacteria. FEMS Microbiol. Rev. 12, 87-108. doi: 10.1111/j.1574-6976.1993.tb00013.x.
Jinneman et al. (2003) Multiplex real-time PCR method to identify shiga toxins, stx1 and sbc2 and *E. coli* O157:H7 Serogroup. Appl. Environ. Microbiol. 69, 6327-6333. doi: 10.1128/AEM.69.10.6327-6333.2003.
Jordan et al. (1999) Survival of low-pH stress by *Escherichia coli* O157:H7: correlation between alterations in the cell envelope and increased acid tolerance. Appl. Environ. Microbiol. 65, 3048-3055.
Karmali (1989) Infection by verotoxin-producing *Escherichia coli*. Clin. Microbiol. Rev. 2, 15-38.
Kudva et al. (1999) Biocontrol of *Escherichia coli* 0157 with O157-specific bacteriophages. Appl. Environ. Microbiol. 65, 3767-3773.
Large et al. (2005) Variation in acid resistance among shiga toxin-producing clones of pathogenic *Escherichia coli*. Appl. Environ. Microbiol. 71, 2493-2500. doi: 10.1128/AEM. 71.5.2493-2500.2005.
Leiman et al. (2004) Three-dimensional rearrangement of proteins in the tail of bacteriophage T4 on infection of its host. Cell 118, 419-429. doi: 10.1016/j.cell.2004.07.022.

(56) References Cited

OTHER PUBLICATIONS

Leuschner et al. (1993) Characterization of a virulent Lactabacillus sake phage PWH2. Appl. Microbiol. Biotechnol. 39, 617-621. doi: 10.1007/BF00205063.

Leyer and Johnson (1993) Acid adaptation induces cross-protection against environmental stress in *Salmonella typhimurium*. Appl. Environ. Microbiol. 59, 1842-184 7.

Leyer et al. (1995). Acid adaptation of *Escherichia coli* O157:117 increases survival in acidic foods. Appl. Environ. Microbil. 61, 3752-3755.

Lin et al. (1996) Mechanisms of acid resistance in enterohemorrhagic *Escherichia coli*. Appl. Environ. Microbiol. 62, 3094-3100.

Lu et al. (2003) Isolation and characterization of a Lactobacillus plantarum bacteriophage JL-1 from a cucumber fermentation. Int. J. Food Microbiol. 84, 225-235. doi: 10.1016/S0168-1605(03)00111-9.

Lu et al. (2005). Sequence analysis of the Lactobacillus plantarum bacteriophage JL-1. Gene 348, 45-54. doi: 10.1016/j.gene.2004.12.052.

Mahony et al. (2011) Bacteriophages as biocontrol agents of food pathogens. Curr. Opin. Biotechnol. 22, 157-163 doi: 10.1016/j.copbio.2010.10.008.

Mead and Griffin (1998) *Escherichia coli* O157:H7. Lancet 352, 1207-1212. doi: 10.1016/S0140-6736(98)01267-7.

Mead et al. (1999) Food-related illness and death in the United States. Emerg. Infect. Dis. 5, 607-625. doi: 10.3201/eid0505.990502.

Mizoguchi et al. (2003) Coevolution of bacteriophage PP01 and *Escherichia coli* O157:H7 in continuous culture. Appl. Environ. Microbiol. 69, 170-176. doi: 10.1128/AEM.69.1.170-176.2003.

Morita et al. (2002) Characterization of a virulent bacteriophage specific for *Escherichia coli* O157:H7 and analysis of its cellular receptor and two tail fiber genes. FEMS Microbiol. Lett. 211, 77-83. doi: 10.1111/j.1574-6968.2002.tb11206.x.

Nataro and Kaper (1998) Diarrheagenic *Escherichia coli*. Clin. Microbiol. Rev. 11, 142-201.

Nechaev and Severinov (2008) The elusive object of desire—interactions of bacteriophages and their hosts. Curr. Opin. Microbiol. 11, 186-193. doi: 10.1016/j.mib.2008.02.009.

O'Flaherty et al. (2009) Bacteriophage and their lysins for elimination of infectious bacteria. FEMS Microbiol. Rev. 33, 801-819. doi: 10.1111/j.1574-6976.2009.00176.x.

O'Flynn et al. (2004) Evaluation of a cocktail of three bacteriophages for biocontrol of *Escherichia coli* O157:H7. Appl. Environ. Microbiol. 70, 3417-3424. doi: 10.1128/AEM.70.6.3417-3424.2004.

Ongeng et al. (2013) Fate of *Escherichia coli* O157:H7 and *Salmonella enterica* in the manure-amended soil-plant ecosystem of fresh vegetable crops: a review. Grit. Rev. Microbiol. doi: 10.3109/1040841X.2013.829415 [Epub ahead of print].

Park et al. (2012) Characterization and comparative genomic analysis of a novel bacteriophage, SFP10, simultaneously inhibiting both *Salmonella enterica* and *Escherichia coli* O157:H7. Appl. Environ. Microbiol. 78, 58-69. doi: 10.1128/AEM.06231-11.

Price et al. (2000) Role of rpoS in acid resistance and fecal shedding of *Escherichia coli* O157:117. Appl. Environ. Microbiol. 66, 632-637. doi: 10.1128/AEM.66.2.632-637.2000.

Price et al. (2004) Acid resistance systems required for survival of *Escherichia coli* O157:H7 in the bovine gastrointestinal tract and in apple cider are different. Appl. Environ. Microbiol. 70, 4 792-4799. doi: 10.1128/AEM.70.8.4792-4799.2004.

Rangel et al. (2005) Epidemiology of *Escherichia coli* O157:H7 outbreaks, United States, 1982-2002. Emerg. Infect. Dis. 11, 603-609. doi: 10.3201/eid1104.040739.

Raya et al. (2006) Isolation and characterization of a new T-even bacteriophage, CEV1, and determination of its potential to reduce *Escherichia coli* O157:H7 levels in sheep. Appl. Environ. Microbiol. 72, 6405-6410. doi: 10.1128/AEM.03011-05.

Remis et al. (1984) Sporadic cases of hemorrhagic colitis associated with *Escherichia coli* O157:H7. Annu. Intern. Med. 101, 728-742. doi: 10.7326/0003-4819-101-5-624.

Riede (1987). Receptor specificity of the short tail fibres (gp12) of T-even type *Escherichia coli* phages. Mo/. Gen. Genet. 206, 110-115. doi: 10.1007/BF00326544.

Riley, et al. (1983) Hemorrhagic colitis associated with a rare *Escherichia coli* serotype O157:H7. N. Engl. J. Med. 308, 681-685. doi: 101056/NEJM198303243081203.

Santos et al. (2011) Genomic and proteomic characterization of the broad-host-range Salmonella phage PVP-SE1: creation of a new phage genus. J. Viral. 85, 11265-11273. doi: 10.1128/JVI.01769-10.

Shahrbabak et al. (2013) Isolation, characterization and complete genome sequence of Phaxl: a phage of *Escherichia coli* O157: H7. Microbiology 159, 1629-1638. doi: 10.1099/mic.0.063776-0.

Sharma (2013) Lytic bacteriophages: potential interventions against enteric bacterial pathogens on produce. Bacteriophage 3, e25518. doi: 10.4161/bact.25518.

Sharma et al. (2009). Effectiveness of bacteriophages in reducing *Escherichia coli* O157:H7 on fresh-cut cantaloupes and lettuces. J. Food Protien 72, 1481-1485.

Sheng et al. (2006). Application of bacteriophages to control intestinal *Escherichia coli* O157:H7 levels in ruminants. Appl. Environ. Microbiol. 72, 5359-5366. doi: 10.1128/AEM.00099-06.

Sheng et al. (2008). Characterization of an *Escherichia coli* O157:H7 O-antigen deletion mutant and effect of the deletion on bacterial persistence in the mouse intestine and colonization at the bovine terminal rectal mucosa. Appl. Environ. Microbiol. 74, 5015-5022. doi: 10.1128/AEM.00743-08.

Swerdlow et al. (1992) a waterborne outbreak in Missouri of *Escherichia coli* O157:H7 associated with bloody diarrhea and death. Annu. Intern. Med. 117, 812-819. doi: 10.7326/0003-4819-117-10-812.

Tanji et al. (2004) Toward rational control of *Escherichia coli* O157:1-17 by a phage cocktail. Appl. Microbiol. Biotechnol. 64, 270-274. doi: 10.1007/s00253-003-1438-9.

Tarr (1995) *Escherichia coli* O157:H7: clinical, diagnostic, and epidemiological aspects of human infection. Clin. Infect. Dis. 20, 1-10. doi: 10.1093/clinids/20.1.1.

Tomat et al. (2013) Phage biocontrol of enteropathogenic and shiga toxin-producing *Escherichia coli* in meat products. Front. Cell. Infect. Microbiol. 3:20. doi: 10.3389/fcimb.2013.00020.

Tuttle et al. (1999) Lessons from a large outbreak of *Escherichia coli* O157:H7 infections: insights into the infectious dose and method of widespread contamination of hamburger patties. Epidemiol. Infect. 122, 185-192. doi: 10.1017/S0950268898001976.

Vasu and Nagaraja (2013) Diverse functions of restriction-modification systems in addition to cellular defense. Microbiol. Mol. Biol. Rev. 77, 53-72. doi: 10.1128/MMBR.00044-12.

Viazis et al. (2011) Reduction of *Escherichia coli* O157:H7 viability on leafy green vegetables by treatment with a bacteriophage mixture and trans-cinnamaldehyde. Food Microbiol. 28, 149-157. doi: 10.1016/j.fm.2010.09.009.

Weagant et al. (1994) Survival of *Escherichia coli* O157:H7 in mayonnaise and mayonnaisebased sauces at room and refrigerated temperatures. J. Food Protein 57, 629-631.

Yu et al. (2000) Characterization of the distal tail fiber locus and determination of the receptor for phage AR1, which specifically infects *Escherichia coli* O157:H7. J. Bacterial. 182, 5962-5968. doi: 10.1128/JB.182.21.5962-5968.2000.

ESCHERICHIA COLI O157:H7 BACTERIOPHAGE Φ241

CROSS-REFERENCE TO RELATED APPLICATIONS

This application is a National Stage of PCT/US2016/027695 filed Apr. 15, 2016, which claims priority to co-pending U.S. application Serial No. 62/148,502 filed Apr. 16, 2015, each of which is expressly incorporated by reference herein in its entirety.

*Escherichia coli* O157:H7 has emerged as one of the major food-borne pathogens. Each year, it causes more than 73,000 illnesses, 2,100 hospitalizations, and 60 deaths in the U.S. (Mead and Griffin, 1998; Mead et al., 1999; Rangel et al., 2005). A variety of foods have been associated with these outbreaks such as undercooked ground beef (Griffin and Tauxe, 1991; Anonymous, 1993, 2014; Bell et al., 1994), raw milk (Riley et al., 1983), cheese (Anonymous, 2010), bologna (Anonymous, 2011), cold sandwiches (Karmali, 1989), water (Swerdlow et al., 1992; Bopp et al., 2003), unpasteurized apple juice (Anonymous, 1996), sprouts, lettuce, spinach, and other vegetables (Como-Sebetti et al., 1997; Jinneman et al., 2003; Anonymous, 2006, 2012a,b, 2013). Healthy cattle are the primary reservoir of *E. coli* O157:H7. Human infection by *E. coli* O157:H7 can frequently be traced to the food or water contaminated with cattle manure (Gyles 2007). The infection by this pathogen can result in severe hemorrhagic colitis and life-threatening hemolytic uremic syndrome (Remis et al., 1984; Cleary, 1988; Tarr, 1995; Nataro and Kaper, 1998). *E. coli* O157:H7 has a very low infectious dose (as low as 10 cells) (Griffin and Tauxe, 1991; Griffin et al., 1994; Tuttle et al., 1999) partly due to its very efficient mechanisms of stress resistance (Price et al., 2004). Acid resistance is one of the characteristics of *E. coli* O157:H7.

*E. coli* O157:H7 has evolved multiple mechanisms to survive in low-pH environments (Lin et al., 1996; Castanie-Cornet et al., 1999; Jordan et al., 1999; Price et al., 2000, 2004; Large et al., 2005) such as gastrointestinal tracts and various acidic foods (Weagant et al., 1994; Diez-Gonzalez and Russell, 1999; Price et al., 2004). Acid resistance is especially crucial for food-borne pathogens that must survive the hostile acidic condition in the stomach before entering and colonizing the small intestines or colon (Berk et al., 2005; Chen and Jiang, 2014).

Acid adaptation can further enhance the survival of *E. coli* O157:H7 in fermented or acidified foods, and induce the cross-protection against heat, salt, and acids (Farber and Pagotto, 1992; Leyer and Johnson, 1993; Leyer et al., 1995; Cheville et al., 1996). A variety of acidic foods have been involved in the outbreaks caused by *E. coli* O157:H7. These include apple cider (Besser et al., 1993; Hilborn et al., 2000), unpasteurized apple juice (Cody et al., 1999), salami (Anonymous, 1995), and fermented sausage (Glass et al., 1992). *E. coli* O157:H7 can also tolerate high concentration of NaCl (Glass et al., 1992).

Many physical, chemical, and biological methods such as pasteurization, radiation, addition of preservatives, or addition of lactic acid bacteria have been used to control *E. coli* O157:H7 in foods. However, these control methods are not very effective for certain foods or they can alter the color, flavor, or texture of the foods. Safe and effective alternative methods are needed to control *E. coli* O157:H7 in foods.

The use of phages to control pathogenic bacteria in foods is a promising novel strategy. The use of phages as antibacterial agents has several advantages over traditional antibacterial methods. Phages are highly host specific. They only infect specific bacterial hosts and cause rapid bacterial lysis. They do not infect humans and other eukaryotes. Phages specific for pathogenic bacteria do not disrupt normal microflora in humans (Kudva et al., 1999) or in animals. Phages are not toxic to humans. Although certain cell lysis may release endotoxins, phages themselves do not generate any toxic products during their multiplication (Hagens and Loessner, 2010). Phages do not alter food quality because they do not produce any substances that can change the taste, composition, aroma, or color of foods. In addition, phages are stable (Coffey et al., 2010), but also self-limiting in foods. They do not replicate unless their bacterial hosts are present (Hagens and Loessner, 2010). Moreover, phages are the most abundant biological entities and naturally present in the environment and a wide variety of foods (Guenther et al., 2009). It is relatively easy to isolate phages from the environment and propagate them in laboratories. All these features make phages promising novel biocontrol agents of bacterial pathogens in foods.

Recent studies have shown high efficacy of using phages against several major food-borne pathogens including *E. coli* O157:H7, *Listeria monocytogenes*, and *Salmonella enterica* in food products or on food contact surfaces. Use of phages specific for *E. coli* O157:H7 resulted in significant, log-unit reductions in *E. coli* O157:H7 counts in a variety of foods such as tomato, spinach, broccoli, and ground beef (Abuladze et al., 2008), beef (Carter et al., 2012), cantaloupe (Sharma et al., 2009), lettuce (Sharma et al., 2009; Ferguson et al., 2013), and other leafy green vegetables (Viazis et al., 2011). Such reductions could substantially decrease a risk of food-borne infections by the pathogen.

Significant progress in phage research for food safety has been made toward phage applications in foods. Several phage-based food additives have been recently approved or cleared by the U.S. Food and Drug Administration (FDA). These approvals have increased the impetus of phage research to uncover phage-mediated applications against other food-borne pathogens (Mahony et al., 2011). It is likely that more phage products will be developed and gradually gain market acceptance by the food industry and the consumers as a means of a safe, natural, and effective prevention of food-borne diseases (O'Flaherty et al., 2009; Sharma, 2013).

Phages specific for *E. coli* O157 have previously been isolated from human fecal materials or animal manures from bovine, ovine, swine, and chicken (Kudva et al., 1999; Morita et al., 2002; O'Flynn et al., 2004; Tomat et al., 2013), lake or pond water (Shahrbabak et al., 2013), and sewage (Sheng et al., 2006; Shahrbabak et al., 2013). No *E. coli* O157-specific phages were isolated from the environment where both acidity and salinity are high.

The inventive method isolated an *E. coli* O157:H7-specific phage from a cucumber fermentation with low pH (3.7) and high salt concentration (5% NaCl), to characterize the phage, and to evaluate the potential of the phage as an effective biocontrol agent against *E. coli* O157:H7 in various foods.

In an embodiment a method for preparing a food item at least substantially free of *E. coli* O157:H7 strain contamination is disclosed. The method comprises contacting the food item with a bacteriophage φ241 under conditions for the bacteriophage φ241 to lyse all or substantially all of the *E. coli* O157:H7 present in the food item while leaving *E. coli* strains other than O157:H7 not affected or substantially not affected. In an embodiment, the food item has a low pH, high salinity, or both. The time of contacting the food item with bacteriophage φ241 for lysis of O157:H7 strain can occur within one hour. The cell lysis may continue for several hours. In another embodiment, the multiplicity of infection is 10, 3, or 0.3. In embodiments, the final phage φ241 concentrations in the foods may reach $5 \times 10^8$ PFU/ml In one embodiment, the food item is vegetable, fruit, meat, dairy, or juice. In other embodiments, the food item may be a food-contact surface, e.g., a utensil, table top, cutting board, food processing equipment, packaging material, etc. The step of contacting may be by direct addition or by spraying the bacteriophage φ241 on the food item. The phage can also be directly added into prepared foods such as many ready-to-eat foods like Deli meat, salad, sandwiches, cheese, and fruits and vegetables.

In one embodiment, the bacteriophage φ241 is in a liquid composition. The phage can be prepared in many liquid foods such as cucumber juice, beef broth, and milk. In one embodiment, the composition is a phage solution with phage particles in cucumber juice, beef broth, or milk at the concentration of $1 \times 10^{10}$ PFU/ml with no other components or additives. In one embodiment, bacteriophage φ241 is provided with another biocontrol additive.

In one embodiment, a method for preparing a food item at least substantially free of *Escherichia coli* O157:H7 strain contamination comprises contacting the food item with bacteriophage φ241 at an initial multiplicity of infection of 10 for a time of about 2 hours at room temperature or 37° C.

In another embodiment, a method for detecting the presence of *Escherichia coli* O157:H7 is disclosed. The method comprises contacting a bacteriophage φ241 with a food item. The contact may be direct addition into or onto the food item. Various phage-based detection assays can be used to detect *E. coli* O157:H7 in foods, water, and other environment. For example, phage replication assay can specifically detect viable O157:H7 cells. Real-time PCR during phage replication can monitor the release of phage DNA from lysed cells. In addition, phage φ241 can be fluorescently labeled and used to discriminate and detect *E. coli* O157:H7 in foods. In another embodiment, the method comprises contacting a bacteriophage φ241 with an item, such as a food item or a food-contact surface, suspected of containing or having *E. coli* O157:H7, and detecting a lysis product from the lysed *E. coli* O157:H7. In one embodiment, the lysis product that is detected is a *E. coli* O157:H7 nucleic acid. In various embodiments, the detected nucleic acid need not necessarily be specific for *E. coli* O157:H7 as the bacteriophage φ241 is specific for *E. coli* O157:H7, as described above, and therefore, detection of *E. coli* nucleic acid would be indicative of the presence of *E. coli* O157:H7. The detected nucleic acid can be DNA or RNA, and its detection is accomplished by methods known in the art. In another embodiment, the lysis product is an intracellular *E. coli* O157:H7 protein, or fragment thereof, and the detection step detects the intracellular protein, or fragment thereof. The *E. coli* O157:H7 protein, or fragment thereof, can be detecting using methods known in the art which detect the presence of the protein, or if the protein is an enzyme, detecting a product of the released enzyme. In one embodiment, the detection method results in a visual signal. For example, when the lysis product is an enzyme, providing a substrate of the enzyme which is conjugated with a color-producing or fluorescence-producing label results in the production of a color or fluorescence. As is known in the art, the label may be a quenched fluorophore, and upon enzymatic action on the substrate, the fluorophore is released and fluoresces. In addition, commercially available kits for detection of *E. coli* O157:H7 may be used, where the required lysis step, usually using lysozyme and/or proteinase K, is replaced with the described phage φ241. Furthermore, phage φ241 may also be used for phage therapy to treat *E. coli* O157:H7 infection in animals and humans.

BACTERIAL STRAINS AND CULTURE CONDITIONS

Figure 1:
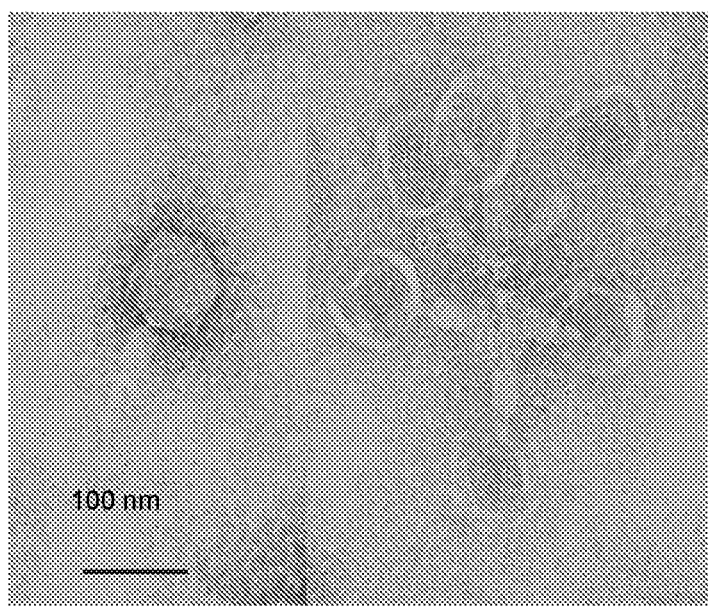
FIG. 1 is a transmission electron micrograph of phage Φ241 negatively stained with 2% uranyl acetate (pH 4), scale bar 100 nm.

*E. coli* strains used are listed in Tables 1 and 2. A total of 46 *E. coli* O157:H7 strains, and 18 *E. coli* non-O157:H7 strains from various sources were obtained from the culture collection of USDA Agricultural Research Service, North Carolina State University. The non-O157 strains included a variety of *E. coli* strains that express a variety of H antigens including H7 antigen. Two previously described O antigen-negative mutants (43895Δper and F12), one per-complemented mutant (43895ΔperComp), and two *E. coli* O157:H7 parent strains (ATCC 43895 and 8624) were kindly provided by Pina Fratamico (Table 3). All strains were stored in tryptic soy broth (TSB; Difco) supplemented with 16% (v/v) glycerol at −80° C. until use. Fresh overnight culture of each *E. coli* strain was prepared by inoculating 10 ml of TSB with an isolated colony from a tryptic soy agar (TSA) plate and incubating statically for 12 h at 37° C. For phage lysate preparation, TSB broth was supplemented with 10 mM $CaCl_2$ (SigmaAldrich, St. Louis Mo., USA) unless otherwise stated. Soft TSA agar used in plaque assay was prepared with TSB broth supplemented with 0.6% agar.

Brine Sample Collection and Treatment

To isolate *E. coli* O157:H7-specific phages, brine samples (40 ml each) were taken from seven industrial cucumber fermentation tanks (capacity: 32,000 l) from a commercial processing plant (the Mount Olive Pickle Company in Raleigh N.C.). The tanks contained approximately 55% pickling cucumbers in 5 to 8% recycled NaCl brine, prepared essentially as described by Breidt et al. (2013). These samples were taken during the fermentation (3-5 days after the tanks were packed and brined). Samples were transported to the laboratory at ambient temperature (~23° C.), stored at 4° C., and processed within 24 h. The pH of each brine sample was measured and adjusted to around 6.4 with 5 M NaOH. The pH-adjusted brine samples were then centrifuged (5,000×g for 10 min). The supernatants were filtered through syringe filters (0.45 μm pore size) to remove cellular materials and solid particles. The filtrates were stored at 4° C. until used as potential phage source for phage isolation.

Phage Isolation

Ten *E. coli* O157:H7 strains (shown in bold text, Table 1) were used as potential hosts for phage isolation. Overnight cultures of these O157 strains (-109 CFU/ml) were prepared in TSB. A 96-well microplate was used to enrich phages potentially present in the filtered brines. Each well of the microplate contained 200 μl of TSB, 5 μl of one of the 10 *E. coli* O157:H7 strains and 45 μl of one of the eight filtered brines, so the eight wells in the same column received the same O157:H7 strain. The first 10 wells in the same row received the same filtered brine. After incubation at 37° C. for 20 h, the microplate was centrifuged (SH-3000 rotor, RC-5B centrifuge, Sorvall, Newtown Conn., USA) at 4,000 rpm, 4° C. for 20 min. The supernatant (lysate) in each well was collected and used in spot tests to detect the presence of phages. Each spot test was performed by adding 10 μl of a phage lysate onto a lawn of *E. coli* O157:H7 in a soft agar overlay on a TSA plate. After overnight incubation at 37° C., the plates were checked for a zone of bacterial lysis.

TABLE 1

*Escherichia coli* O157:H7 strains that are sensitive to phage φ241.

| Id[a] | Serotype | Source |
|---|---|---|
| B0201[b] | O157:H7 | Apple cider outbreak |
| B0349 | O157:H7 | Spinach outbreak |
| B0264 | O157:H7 | Apple juice outbreak, 1996 |
| B0204 | O157:H7 | Pork |
| B0202 | O157:H7 | Salami outbreak |
| B0203 | O157:H7 | Ground beef |
| B0348 | O157:H7 | Salami |
| B0350 | O157:H7 | Sakai |
| B0243 | O157:H7 | Bovine carcass |
| B0242 | O157:H7 | Bovine carcass |
| B0240 | O157:H7 | Bovine carcass |
| B0239 | O157:H7 | Bovine carcass |
| B0238 | O157:H7 | Bovine carcass |
| B0241 | O157:H7 | Bovine carcass |
| B0258 | O157:H7 | Bovine feces |
| B0259 | O157:H7 | Bovine feces |
| B0301 | O157:H7 | Water |
| B0307 | O157:H7 | Water |
| B0306 | O157:H7 | Water |
| B0309 | O157:H7 | Water |
| B0302 | O157:H7 | Water |
| B0297 | O157:H7 | Water |
| B0299 | O157:H7 | Water |
| B0285 | O157:H7 | Water |
| B0275 | O157:H7 | Water |
| B0305 | O157:H7 | Water |
| B0281 | O157:H7 | Water |
| B0289 | O157:H7 | Water |
| B0280 | O157:H7 | Water |
| B0287 | O157:H7 | Water |
| B0283 | O157:H7 | Water |
| B0269 | O157:H7 | Human, outbreak, 2000, waterborne |
| B0273 | O157:H7 | Human, outbreak, 2002, leafy vegetable |
| B0247 | O157:H7 | Human, outbreak |
| B0296 | O157:H7 | Human, outbreak, 2006, leafy vegetable |
| B0311 | O157:H7 | Human, outbreak, 2006, leafy vegetable |
| B0246 | O157:H7 | Human, outbreak |
| B0271 | O157:H7 | Human, outbreak, 2003, leafy vegetable |
| B0250 | O157:H7 | Human, outbreak |
| B0263 | O157:H7 | Human, sporadic, 1997 |
| B0251 | O157:H7 | Human, outbreak |
| B0249 | O157:H7 | Human, outbreak |
| B0266 | O157:H7 | Human, outbreak, 1999, taco meat |
| B0245 | O157:H7 | Human, outbreak |
| B0265 | O157:H7 | Human, outbreak, 1999, lettuce |
| B0244 | O157:H7 | Human, outbreak |

[a]ID, identification number in the culture collection of USDA-ARS Food Fermentation Laboratory.
[b]The strains with ID bolded were used for initial phage isolation.

TABLE 2

Non-O157 strains of *E. coli* that are resistant to phage φ241.

| B0445 | O26:H11 | Human |
|---|---|---|
| B0449 | O25:H11 | Human |
| B0463 | O103:H6 | Human diarrhea |
| B0460 | O103:H25 | Human |
| B0469 | O103:H4 | Human |
| B0467 | O104:H21 | Human, milk outbreak |
| B0475 | O111:NM[b] | Human |
| B0478 | O111:H8 | Human |
| B0479 | O121:NM | Human diarrhea |
| B0485 | O145:NM | Human |
| B0457 | O45:H2 | Cow (calf) |
| B0468 | O104:H7 | Ground beef |
| B0235 | Non-O157[c] | Bovine feces |
| B0237 | Non-O157 | Bovine feces |
| B0234 | Non-O157 | Bovine feces |
| B0236 | Non-O157 | Bovine feces |
| B0233 | Non-O157 | Bovuie feces |
| 25922 | O6:H1 | ATCC[d] |

[a]ID, identification number.
[b]NM, non-motile.
[c]The strains were not completely serotyped. But the data showed that they did not respond to the serum antibody against O157 strains.
[d]ATCC, American type Culture Collection.

Phage Purification and Concentration

Phage from a positive spot-test plate was purified and concentrated using the methods described by Lu et al. (2003) with minor modification. Briefly, an isolated single plaque was picked and propagated against its natural host in TSB at 37° C. After two runs of plaque purification, the phage lysate was prepared and then centrifuged at 5,000×g for 10 min. The supernatant was filtered through bottle-top filter (0.45 μm pore size). The filtered high titer phage stock (typically ca. $10^{10}$ PFU/ml) was stored at 4° C. To further purify and concentrate the phage, a portion of the phage stock were treated with DNase I and RNase A, and then concentrated by PEG precipitation. The concentrated phage was further purified by CsCI step density gradient ultracentrifugation at 600,000×g for 6 h at 4° C. followed by dialysis as described by Lu et al. (2003). The ultracentrifuge-purified phage was used for electron microscopy analysis, SDS-PAGE, and DNA extraction.

Electron Microscopy

Phage samples were negatively stained with 2% (w/v) aqueous uranyl acetate (pH 4) on carbon-coated grids and examined by transmission electron microscopy (JEM 1200EX TEM, JEOL) at an accelerating voltage of 80 kV. Electron micrographs were taken at a magnification of 50,000× (Center for Electron Microscopy, North Carolina State University, Raleigh N.C., USA).

TABLE 3

Phage susceptibility of E. coli O157:H7 strains and their O antigen-negative mutants.

| E coli strain | Description | Plaque formation[a] | Source or reference |
|---|---|---|---|
| ATCC 43895 | Wild-type E. coli O157:H7, clinical isolate, $stx_1^+/stx_2^+$ | + | ATCC[b] |
| 43895Δper | O antigen-negative mutant of ATCC 43895 with perosamine synthetase deleted | − | Sheng et al. (2008) |
| 43895Δper Comp | 43895Δper tranformed with pCRII::per | + | Sheng et al. (2008) |
| 8624 | Wild-tyupe E. coli O157:H7, clinical isolate, $stx_1^+/stx_2^+$ | + | Bilge et al. (1996) |
| F12 | O antigen-negative mutant of strain 8624 | − | Bilge et al. (1996) |

[a]+, susceptible to φ241; −, not susceptible to φ241.
[b]ATCC, American type Culture Collection.

One-Step Growth Kinetics

One step growth experiments were carried out based on the method described by Leuschner et al. (1993) and Foschino et al. (1995) with some modifications. Briefly, the experiment started at a multiplicity of infection (MOI) of 0.01 in a 15-ml tube containing the phage (approximately $1 \times 10^6$ PFU/ml) and its natural host O157:H7 strain B0241 in 10 ml TSB. After incubation in a water bath at 37° C. for 10 min (to allow phage adsorption), the tube was centrifuged at 13,000×g for 30 s. The supernatant was removed and subjected to plaque assay to determine the titer of the un-absorbed phage. The pellet containing (partially) infected cells was immediately re-suspended in 10 ml of pre-warmed TSB. After taking the first sample, the tube was returned to the water bath (37° C.). A sample (100 μl) was collected every 5 min (up to 60 min). Each sample was immediately diluted and subjected to plaque assay. All assays were carried out in triplicate. The experiment was repeated three times. Latent period was defined as the time interval between the end of the adsorption and the beginning of the first burst, as indicated by the initial rise in phage titer (Ellis and Delbruck, 1939; Adams, 1959). Burst size was calculated as the ratio of the final number of liberated phage particles to the initial number of infected bacterial cells during the latent period (Adams, 1959).

Host Range

Phage Φ241 was the only phage isolated from one of the seven samples. The host range of Φ241 was determined by spot tests against 46 E. coli O157:H7 strains (Table 1) and 18 non-O157 strains (Table 2) on TSA. In each test, 10 μl of high titer phage stock ($10^{10}$ PFU/ml) was used to spot a bacterial lawn of a strain on a plate. Each test was done in duplicate. The O antigen-negative mutants of E. coli O157:H7 and their parent strains (Table 3) were also tested using the agar overlay method.

Phage Structural Proteins

The phage structural proteins were analyzed using the method previously described by Lu et al. (2003) with some modifications. Briefly, the ultracentrifuge-purified phage particles were mixed with SDS-PAGE sample buffer and then heated in a boiling water bath for 10 min. The boiled sample was loaded onto a NuPAGE precast gradient minigel (4-12% Bis-Tris, Invitrogen Corporation, Carlsbad Calif., USA). Electrophoresis was carried out at 75 V for 2 h. Pre-stained protein standard (Invitrogen) was used to estimate the molecular weights of the proteins. The gel was stained with SimplyBlue SafeStain (Invitrogen).

Phage DNA Extraction and Restriction

Phage DNA was prepared from the concentrated lysate using the phenolchloroform extraction method as described by Lu et al. (2003), and digested with restriction endonucleases (AluI, BamHI, ClaI, EcoRI, EcoRV, HindIII, MspI, SwaI, and XbaI; New England BioLabs, Beverly Mass., USA) according to manufacturer's instructions. The resulting DNA fragments were separated on the 1% agarose gel containing 0.001% SYBR Safe DNA gel stain (Invitrogen) by gel electrophoresis in Tris-borate-EDTA buffer at 70 V for 2 h. The 1 kb DNA ladder (Promega, Madison Wisc., USA) was used to estimate the size of the digested phage DNA.

Phage Infection

The lytic activity of phage Φ241 against host E. coli O157:H7 B0241 was investigated in TSB medium at three different MOIs. A bacterial overnight culture was diluted with TSB to a concentration of ca. $9 \times 10^6$ CFU/ml. Ten milliliter of the diluted bacterial culture was then transferred into each of the four 15-ml tubes. One of these tubes served as a control. To each of other three tubes, a high titer phage stock ($2.8 \times 10^{10}$ PFU/ml) was added to achieve an initial MOI of 10, 3, or 0.3, respectively. The four tubes were incubated statically at 37° C. Samples were taken from each tube at 60-min intervals for a 12-h period. After serial dilution, each sample was plated onto TSA plates using a spiral autoplater (Model 4000, Spiral Biotech, Bethesda, Md., USA). The plates were incubated at 37° C. overnight. The colonies on each plate were enumerated using Q-Count system (Model 510, Spiral Biotech, Norwood Mass., USA). The experiment was repeated two more times.

Statistical Analysis

Differences in bacterial cell concentration between various grouping of MOIs were analyzed by using one-way analysis of variance (ANOVA) and Tukey's multiple comparison.

Isolation of Phage Φ241

Seven brine samples from 32,000-l cucumber fermentation tanks (all from the same commercial plant) were enriched for phage isolation. One sample was found to contain a phage that infects E. coli O157:H7. The phage-containing sample was taken from a tank 3 days after the tank was packed with size 2A cucumbers (~27-32 mm in diameter). The pH and the salt (NaCl) concentration of the sample were 3.7 and 5%, respectively. In contrast, the pH and salt concentration of the samples from other six tanks were in the range of 3.42-3.92, and 6 to 8%, respectively. The higher salinity in these six tanks may greatly inhibit phages, which may explain why no O157:H7 phages were isolated from them. The isolated O157:H7 phage was designated Φ241. The presence of phage Φ241 specifically active against E. coli O157:H7 in an early stage of the commercial cucumber fermentation indicates that the host strain(s) may be present as well. The most likely source for E. coli O157:H7 in the commercial fermentation was the fresh cucumbers. Application of animal waste as fertilizer and irrigation of crops with waste water have been recognized as important routes through which E. coli O157:H7 can contaminate fresh vegetables during primary production (Ongeng et al., 2013). However, we are unaware of any reports of disease outbreaks caused by vegetative pathogens from fermented vegetables. Previous research has shown that E. coli O157:H7 will be killed during fermentation of cucumbers in a pH and time dependent manner (Breidt and Caldwell, 2011).

The isolated phage Φ241 formed small (ca. 1 mm in diameter) plaques on the lawn of its natural host, E. coli O157:H7 strain B0241 which contained stx2 gene and was originally isolated from bovine carcass (Table 1). The concentration of high-titer phage stock (ca. $10^{10}$ PFU/ml) remained unchanged during two years of storage at a refrigeration temperature, indicating that the phage was very stable.

Morphology

The electron micrograph (FIG. 1) showed that phage Φ241 has an icosahedral head (about 80 nm in diameter) and a contractile tail (ca. 33 nm long in the contracted state) with a base plate and several tail fibers. The overall morphology of Φ241 indicated it was a T4-like phage, belonging to the Myoviridae family of the Caudovirales order. Several phage particles appeared to cluster together through the tail fibers (FIG. 1). The base plate and tail fibers are usually involved in the host cell recognition and receptor-binding by many tailed phages (Riede, 1987; Leiman et al., 2004; Bartual et al., 2010; Garcia-Doval and van Raaij, 2012).

One-Step Growth Kinetics

Figure 2:
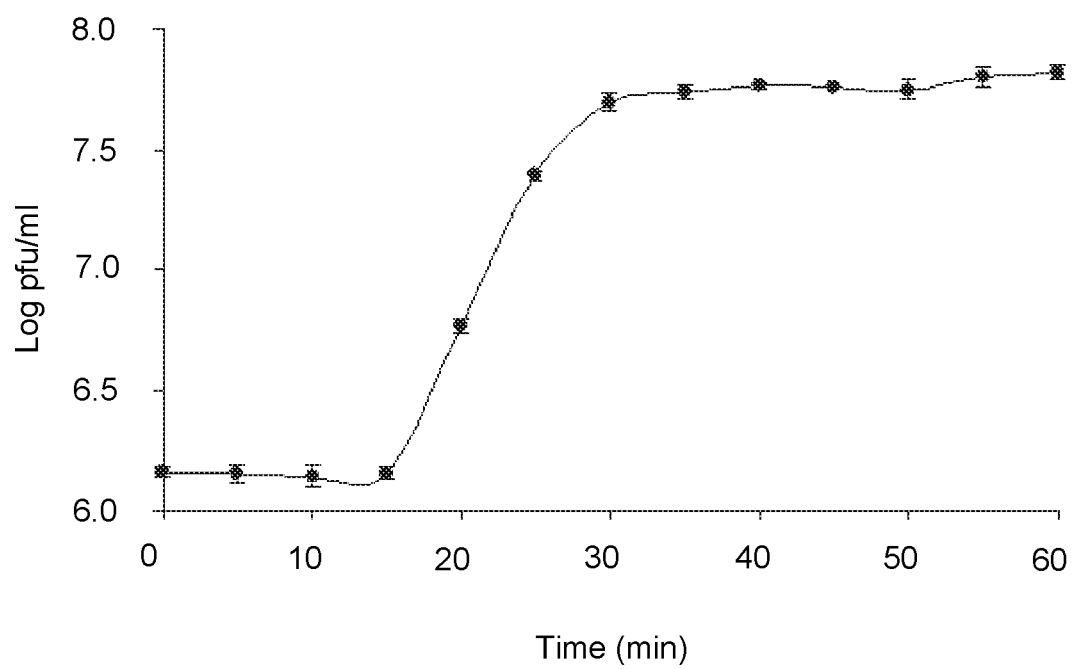
FIG. 2 shows a one-step growth curve of phage Φ241 infecting *E. coli* O157:H7 at MOI 0.01 in TSB medium at 37° C.; the latent period is 15 min and the burst size is about 53 phage particles per infected cell; error bars indicate standard deviations.

FIG. 2 shows the one-step growth of phage Φ241. The latent period was only 15 min (excluding 10 min for adsorption), which was shorter than the typical latent periods (21-120 min) for most Myoviridae phages. A short latent period allows phage Φ241 to replicate faster than most Myoviridae phages. The average burst size of Φ241 was about 53 phage particles per infected cell, which is in the range of 50-100 PFU/cell for many Myoviridae phages (Foschino et al., 1995; Chang et al., 2005; Raya et al., 2006; Bao et al., 2011; Park et al., 2012). A few Myoviridae phages have very large burst sizes. The burst size of phage PhaxI (another O157:H7 phage) is 420 PFU per cell (Shahrbabak et al., 2013). A phage with both a short latent period (15 min or less) and a large burst size (>50 PFU/cell) may have a selective advantage over competing phages, resulting in very high lytic activity (Park et al., 2012).

Host Range

A total of 69 E. coli strains from various sources (Tables 1-3) were tested to determine the host range of phage Φ241. The phage was able to lyse all 46 O157:H7 strains (Table 1), but none of the 18 non-O157 strains (Table 2) including O104:H7 strain which has the same H antigen as that of O157:H7. E. coli O104:H7 was originally isolated from ground beef (Bosilevac and Koohmaraie, 2011). It is also Shiga toxin-producing strain containing two uncommon Shiga toxin gene variants, $stx_{1c}$ and $stx_{2c}$ (Bosilevac and Koohmaraie, 2011). The data suggested that the phage is O157 antigen specific, and H7 antigen may not be involved in the host recognition and binding. Phage infection requires specific receptors on bacterial cells. The common receptors on E. coli include O antigen of lipopolysaccharide (LPS), outer membrane proteins, pili, fimbriae, and flagella (H) antigen (Topley and Wilson, 1990; Bokete et al., 1997). Many cell wall receptors can be shared by different bacterial strains and serotypes (Topley and Wilson, 1990). To confirm that O157 antigen (not H7 antigen) serves as the receptor during Φ241 adsorption, two previously described O antigen-negative mutants (43895Δper and F12), one per-complemented mutant (43895ΔperComp), and two E. coli O157:H7 parent strains (ATCC 43895 and 8624) were tested for their susceptibility to Φ241 infection (Table 3). The mutant 43895Δper was generated by deletion of a putative perosamine synthetase gene (per) in the rfb gene cluster (Sheng et al., 2008). The mutant F12 was created by transposon insertion of TnphoA in the per gene (Bilge et al., 1996). Deletion of per gene or insertion in per gene resulted in a mutant lacking the O antigen. The Δper mutant (43895Δper) also lacked H7 antigen, but the transposon insertion mutant (F12) still expressed the H7 antigen. The per-complemented mutant (43895ΔperComp) was constructed by cloning per in the E. coli vector pCRII and transforming pCRII::per into the mutant to restore O157 antigenicity (Sheng et al., 2008). Table 3 showed that phage Φ241 lysed the two O157:H7 parent strains (ATCC 43895 and 8624) which had the full-length O157 antigen, and the per-complemented strain (43895ΔperComp) which was able to express O157 antigen. The phage did not lyse the two O157 antigen-negative mutants, 43895Δper (also lacking H7 antigen) and F12 (still having H7 antigen). These results indicated that O157 antigen was required for the infection by phage Φ241, and strains lacking O157 antigen were resistant to the phage infection, regardless of the presence or absence of H7 antigen in the strains. Similar observations have been reported for other O157-specific phages. Kudva et al. (1999) studied three O157-specific phages isolated from bovine and ovine fecal samples. They found that the three phages lysed all of the eight tested E. coli O157 strains including the strain 8624 and did not lyse non-O157 E. coli strains, or O157-negative mutants including F12. In addition, the three phages did not lyse the complement of the O157-deficient mutant, F12(pF12), which produces a truncated O157 LPS (Kudva et al., 1999). They found that phage infection and plaque formation were influenced by the structure of the host cell O157 LPS. Strains that did not express the O157 antigen or expressed a truncated LPS were not susceptible to plaque formation or lysis by phage. Strains that expressed abundant mid-range-molecular-weight LPS were lysed in broth media but did not support plaque formation. They explained that in broth media, the excess mid-range-molecular-weight LPS can diffuse from cells into the broth. But on soft agar, those molecules may accumulate around cells, thereby preventing phage attachment (Kudva et al., 1999). An appropriate length of the O side chains and an optimal LPS concentration may be necessary to make the receptor available for phage interaction and/or to allow irreversible phage binding (Calendar, 1988). The high specificity of phage Φ241 for O157 antigen makes it an ideal biocontrol agent of E. coli O157:H7 without disrupting the beneficial bacteria such as probiotics in foods, normal flora in humans, or other microflora in cattle.

Structural Proteins

Figure 3:
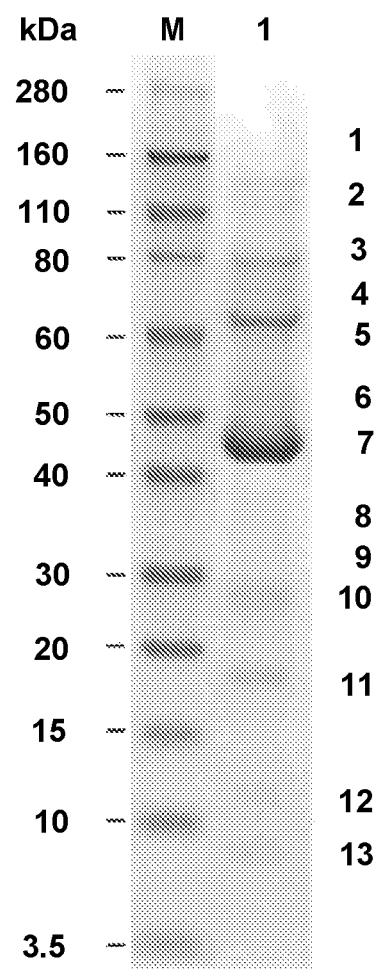
FIG. 3 is an SDS-PAGE of Φ241 structural proteins: Lane M: molecular weight standard; lane 1: Φ241; molecular weights of protein bands in the standard are indicated on the left.

SDS-PAGE gel revealed at least 13 protein bands from Φ241 (FIG. 3), indicating that the phage contained many types of structural proteins. Four of the protein bands are in the molecular weight (MW) range of 26 to 50 kDa. These include three weak bands and one strong band (band 7 in FIG. 3, MW≈44 kDa). This strong band was the strongest one among all bands, indicating that the protein in this band was the most abundant protein. In many tailed phages, the most abundant proteins are usually identified as the major head proteins (Santos et al., 2011). The MWs of major head proteins generally fall within the range of 26-50 kDa. For example, the sequence-predicted MWs of the major capsid protein in Lactobacillus plantarum phage ΦJL-1 (Lu et al., 2005), O157:H7 phage PhaxI (Shahrbabak et al., 2013), Pseudomonas aeruginosa phages LKA1 and LKD16 (Ceyssens et al., 2006), Salmonella enterica phage PVP-SE1 (Santos et al., 2011) are 30.4, 48.0, 36.7, 37.7, and 38.5 kDa, respectively.

DNA Restriction

Figure 4:
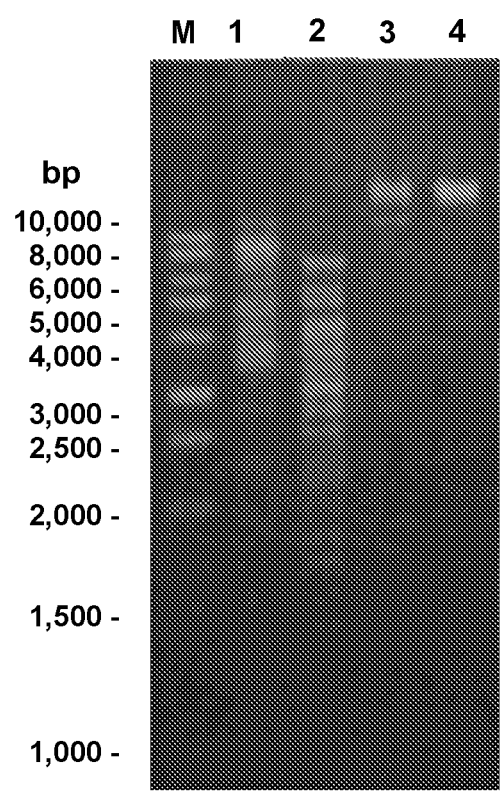
FIG. 4 is a restriction analysis of the DNA from Φ241: Lane M: 1-kb ladder; Lane 1: digestion by AluI; lane 2: digestion by MspI; lane 3: digestion by SwaI; lane 4: undigested DNA.

The Φ241 genome could be digested by rare-cutters, AluI, MspI, and SwaI (FIG. 4). Restriction by AluI or MspI generated more than 15 bands on agarose gel while restriction by SwaI only generated a single band with a high MW. The phage genome could not be digested by many commonly used restriction endonucleases such as BamHI, ClaI, EcoRI, EcoRV, HindIII, and XbaI. Similar phenomenon was also observed for other O157:H7-specific phages. Shahrbabak et al. (2013) reported that the genome of phage PhaxI was resistant to eight tested restriction endonucleases including BamHI, EcoRI, EcoRV, HindIII, and a few others (Shahrbabak et al., 2013). The resistance suggested the presence of modification such as methylation and glycosylation in the phage DNA, allowing the phage to evade the restriction by the host enzymes (Bickle and Kruger, 1993; Nechaev and Severinov, 2008; Vasu and Nagaraja, 2013). Sequence analysis may provide insight into the anti-restriction modification system in phage genome.

Phage Infection

Figure 5:
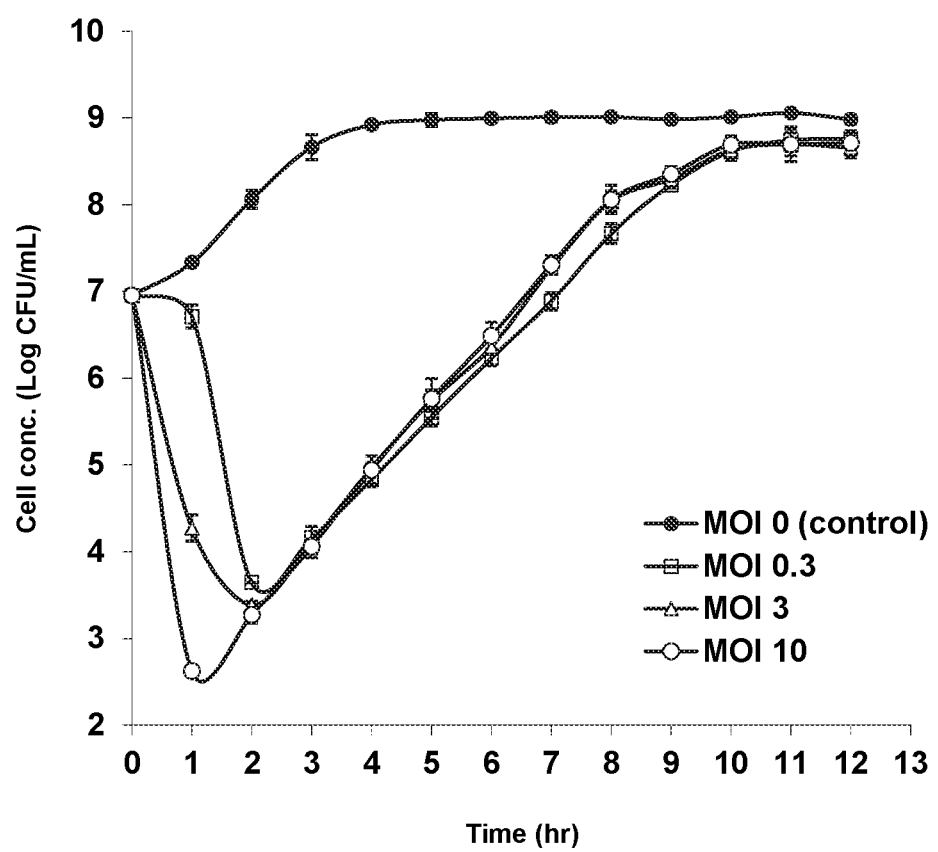
FIG. 5 shows lytic activity of phage Φ241 against *E. coli* O157:H7 in TSB medium at MOI 0 (control), 0.3, 3, or 10; all cultures were incubated at 37° C.; error bars indicate standard deviations in triplicate experiments.

The lytic activity of phage Φ241 against its natural host E. coli O157:H7 B0241 was investigated at three different MOIs. FIG. 5 shows the growth curves of phage-free and phage-infected cultures in TSB medium at 37° C. The phage-free culture (the control culture) grew steadily during the first 4 h of incubation. After 4 h, the control culture entered the stationary phase and remained unchanged (FIG. 5). In contrast, the phage infection at the MOI of 3 or 10 caused a rapid cell lysis within 1 h, resulting in 3- or 4.5-log decrease in the cell concentration. Such a high lytic activity within 1 h may be attributed in part to the short latent period (15 min) of the phage. During the second hour, the cell concentration of the culture with a MOI of 3 continued to decrease while the cell concentration of the culture with the MOI of 10 started to increase. In contrast, infection at the MOI of 0.3 initially caused a slow cell lysis (less than 0.5-log reduction) during the first hour, but a rapid cell lysis (3-log reduction) during the second hour. The data from statistical analysis showed that at 1 h after phage infection the cell concentrations from different MOIs were statistically different ($P<0.05$) and every cell concentration was different from all other cell concentrations ($\alpha=0.05$). At 2 h after phage infection the cell concentration from the MOI of 0.3 was statistically different from all other cell concentrations while the cell concentrations from the initial MOIs of 3 and 10 were not statistically different. Similar rapid cell lysis caused by Φ241 in cucumber juice was also observed (preliminary data not shown). Kudva et al. (1999) evaluated the lytic activity of three O157-specific phages in Luria-Bertani medium supplemented with 5 mM $MgSO_4$ at 37° C. They reported that the significant (>4 log) decrease in E. coli O157:H7 concentration caused by those phages individually or in cocktail required much higher MOI ($10^3$ PFU/CFU) and much longer incubation time (8 h) compared with those in our study. FIG. 5 showed that the cultures with an initial MOI of 3 or 0.3 started to grow after 2 h. After 3 h of infection, all three phage-infected cultures, regardless of the initial MOI, reached the same cell concentration ($10^4$ CFU/ml), which was 4.5-log lower than that of the control and 3-log lower than the initial cell concentration. As the incubation continued, the three cultures continued to grow at a similar rate, gradually approaching to the cell concentration of the control. After 12 h of infection, the phage titers in the cultures at the initial MOI of 10, 3, and 0.3 reached $4\times10^9$, $5\times10^9$, and $1.6\times10^{10}$ PFU/ml, respectively. The culture started with the lowest initial MOI (0.3) contained the highest phage titer ($1.6\times10^{10}$ PFU/ml) at the end of incubation.

The growth of phage-infected cultures after 1 or 2 h of infection indicated that phage-resistant mutants had emerged. The emergence of phage-resistant mutants during phage infection has been reported by many other studies (Kudva et al., 1999; O'Flynn et al., 2004; Park et al., 2012; Tomat et al., 2013). Phage resistance may result from mutation that alters cell surface receptors, restriction modification, or abortive infection associated with the presence of clustered regularly interspaced short palindromic repeats (CRISPRs) in the bacterial genome (Hill, 1993; Hashemolhosseini et al., 1994; Allison and Klaenhammer, 1998; Barrangou et al., 2007). A few studies found that certain phage resistant mutants of E. coli O157:H7 had altered OmpC expression or lost OmpC, suggesting the involvement of the major outer membrane protein in phage attachment (Yu et al., 2000; Morita et al., 2002; Mizoguchi et al., 2003). Some studies found that cell morphology and colony morphology of phage-resistant mutants differed greatly from those of the parent E. coli O157:H7 strains (Mizoguchi et al., 2003; O'Flynn et al., 2004). Phage-resistant mutant cells appeared coccoid and smaller. As a result, phage-resistant culture could not reach the same turbidity as that of the parent strain culture (O'Flynn et al., 2004). The frequency of phage-resistant mutation is generally around $10^{-6}$ CFU for E. coli O157:H7 (O'Flynn et al., 2004; Park et al., 2012; Tomat et al., 2013). With such a low mutation frequency and the low level of E. coli O157:H7 typically encountered in foods, phage resistance should not hinder the use of phages as biocontrol agents against the pathogenic bacteria (O'Flynn et al., 2004; Tanji et al., 2004). Some studies explored the potential of using a phage cocktail to minimize the development of phage resistant mutants on meats and other foods (O'Flynn et al., 2004; Tanji et al., 2004; Carter et al., 2012; Tomat et al., 2013). Using a phage cocktail containing different phages against the same bacterial species can decrease the likelihood of selecting phage-resistant mutants. Because different phages may attach to different receptors on the host, mutations in one phage receptor gene may not alter the mutant's susceptibility to another phage that attaches to a different receptor on the bacterial cells (Tanji et al., 2004).

Phage Φ241 was highly specific for E. coli O157:H7 and very stable when stored at high titers at refrigeration temperature. The phage caused rapid cell lysis, and tolerates both low pH and high salinity. These features indicated that the phage has a high potential as an effective biocontrol agent of E. coli O157:H7 in foods. To our knowledge, this is the first report on the E. coli O157:H7 phage isolated from low pH and high salinity environment.

Figure 6:
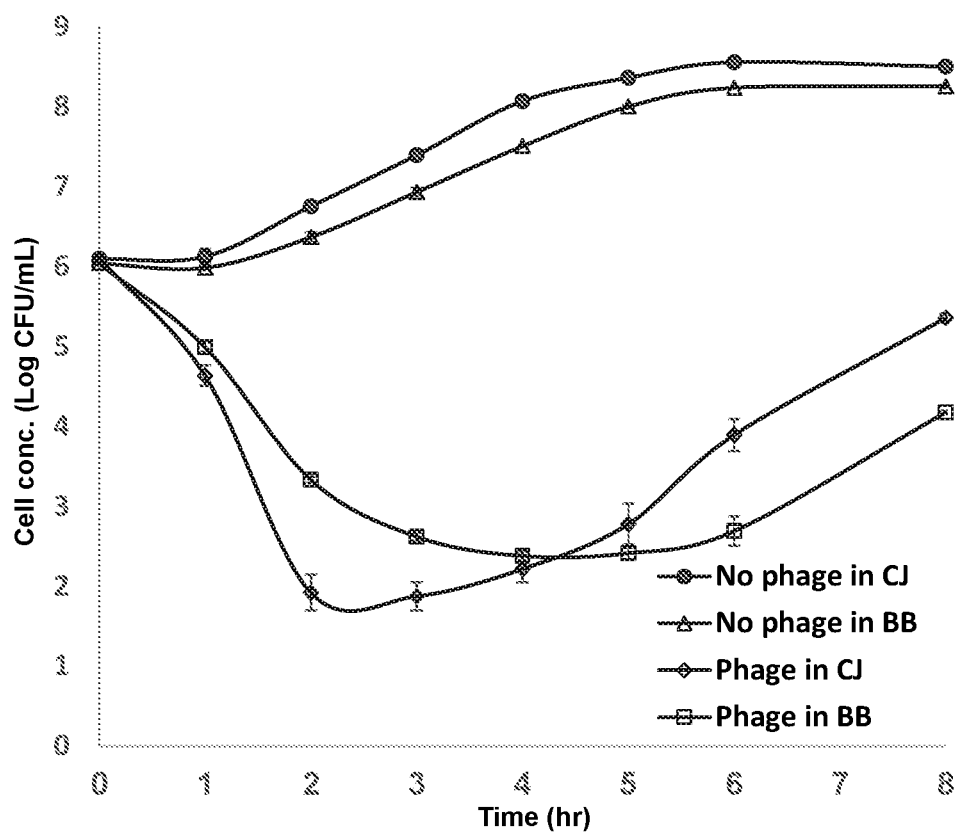
FIG. 6 shows the effect of phage Φ241 at MOI 10 on *E. coli* O157:H7 in cucumber juice (CJ) and beef broth (BB).

The lytic effects of phage ϕ241 infection on the bacterial pathogen E. coli O157:H7 were evaluated in model food systems with cucumber juice (CJ) representing vegetables, and beef broth (BB) representing meats. FIG. 6 showed that in the absence of the phage, E. coli O157:H7 grew exponentially in CJ during the first 4-hour incubation at 37° C., resulting in a rapid increase in cell concentration. After the bacterial population entered the stationary phase, the cell concentration reached $3\times10^8$ cfu/ml, which was more than 2-log units, or more than 100 times, higher than the initial cell concentration. The similar trend of the bacterial growth was also observed in BB although the cell concentration was slightly lower than that in CJ. In contrast, phage infection at MOI 10 caused rapid cell lysis within 2 hr, resulting in 4- and 2.7-log reductions in cell concentrations in CJ and BB, respectively. That is, the phage infection killed 99.99% of cells in CJ and more than 99.5% of cells in BB within 2 hrs. After 3 hr incubation, the cell concentration in CJ started to increase, but the cell concentration was still 3-log units lower than the initial cell concentration or 5.3-log units lower than that in the CJ without phage after 5 h hours. Cell concentration in BB containing phage did not increase during the 6-hr of incubation and maintained more than 5-log units below that in the BB without phage. After 8-hr incubation, the final cell concentrations in the phage containing CJ and BB were $5.4 \times 10^5$ and $1.5 \times 10^4$ cfu/ml, respectively, which were 0.7-log or 1.8-log units lower than the initial cell concentrations ($1 \times 10^6$ cfu/ml) and more than 3- or 4-log units (1,000 or 10,000 times) lower than those in the controls ($3 \times 10^8$ cfu/ml). These results indicated that phage ϕ241 effectively killed the majority of its host cells and greatly inhibited the growth of the pathogen in these model food systems.

Figure 7:
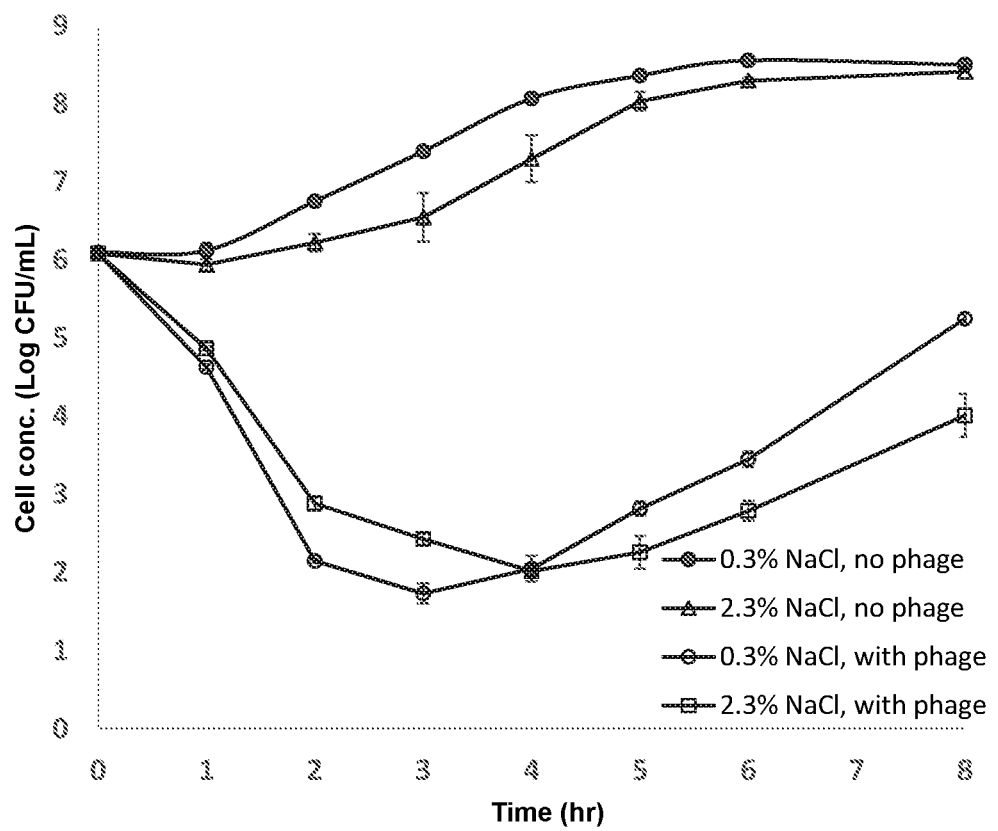
FIG. 7 shows the effect of phage Φ241 at MOI 10 on *E. coli* O157:H7 in cucumber juice supplemented with 2% NaCl.

Since phage ϕ241 was originally isolated from high salinity environment, the lytic effect of the phage on the bacterial pathogen was further evaluated in cucumber juice supplemented with 2% NaCl. FIG. 7 shows that in the absence of the phage, *E. coli* O157:H7 grew rapidly in CJ at 0.3% NaCl (natural salt concentration in cucumber) during the first 4-hr incubation at 37° C. and its concentration increased exponentially before the population entered the stationary phase. A similar growth pattern was also observed in the CJ supplemented with 2% NaCl (totally 2.3% NaCl) although the growth was slower due to the inhibitory effect from the salt. *E. coli* O157:H7 eventually adapted to 2.3% NaCl and reached the same final cell concentration ($3 \times 10^8$ cfu/ml) as that in the natural CJ (without added salt). In contrast, a rapid cell lysis was observed in the presence of phage at MOI 10 within 2 to 3 hours, resulting in more than 3- or 4-log reductions in cell concentration in CJ with 2.3% or 0.3% NaCl. That is, within 2 to 3 hours the phage killed 99.9% of bacterial cells in CJ with 2% added salt and 99.99% of the bacterial cells in CJ without added salt. After 5-hr incubation, the cell concentrations in both phage-containing CJs increased. But the cell concentrations were still more than 3-log units lower than the initial cell concentrations, and more than 5-log units lower than those in CJs without phage. After 8-hr phage infection, the cell concentrations ($1.8 \times 10^5$ in CJ without added salt and $4 \times 10^4$ cfu/ml in CJ with added salt) were still much lower than the initial cell concentration ($1 \times 10^6$ cfu/ml), and more than 3- or 4-log units lower than that ($3 \times 10^8$ cfu/ml) in CJs without phage. The cell concentrations in CJ containing no phage was 1000-10,000 times higher than those in CJs containing the phage. Such a huge difference in cell concentrations clearly showed that phage ϕ241 not only tolerated 2.3% salt, but also effectively killed most of the bacterial cells and significantly inhibited the growth of the bacterial pathogen in the salty food. Phage ϕ241 may have the same or similar effect on *E. coli* O157:H7 in other salty foods such as cottage cheese, deli meats, cured meats, certain fish, pasta dishes, and soup.

Infection by phage ϕ241 effectively killed more than 99.9-99.99% of the bacterial cells within 2-3 hr, and greatly inhibited the growth of the pathogen in the model food systems including a salty food. Phage ϕ241 has a high potential and wide application as a biocontrol agent of the bacterial pathogen *E. coli* O157:H7 in various foods, thereby ensuring food safety.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety:

Abuladze et al. (2008). Bacteriophages reduce experimental contamination of hard surfaces, tomato, spinach, broccoli, and ground beef by *Escherichia coli* O157:H7. *Appl. Environ. Microbiol.* 74, 6230-6238. doi: 10.1128/AEM.01465-08

Adams (1959). *Bacteriophage*. New York: Interscience Publishers, Inc.

Allison and Klaenhammer (1998). Phage resistance mechanisms in lactic acid bacteria. *Int. Dairy J.* 8, 207-226. doi: 10.1016/S0958-6946(98)00043-0

Anonymous. (1993). Update: multistate outbreak of *Escherichia coli* O157:H7 infections from hamburgers-Western United States, 1992-1993. *Morb. Mortal. Wkly. Rep.* 42, 258-263.

Anonymous. (1995). *Escherichia coli* O157:H7 outbreak linked to commercially distributed dry-cured salami. *Morb. Mortal. Wkly. Rep.* 44, 157-160.

Anonymous. (1996). Outbreak of *Escherichia coli* O157:H7 infections associated with drinking unpasteurized commercial apple juice—British Columbia, California, Colorado, and Washington, October 1996. *Morb. Mortal. Wkly. Rep.* 45, 975.

Anonymous. (2006). Ongoing multistate outbreak of *Escherichia coli* serotype O157:H7 infections associated with consumption of fresh spinach—United States, September 2006. *Morb. Mortal. Wkly. Rep.* 55, 1045-1046.

Anonymous. (2010). *Investigation Update: Multistate Outbreak of E. coli O157:H7 Infections Associated with Cheese*. Available at: http://www.cdc.gov/ecoli/2010/cheese0157/index.html [accessed Jan. 17, 2015].

Anonymous. (2011). *Investigation Announcement: Multistate Outbreak of E. coli O157:H7 Infections Associated with Lebanon Bologna*. Available at: http://www.cdc.gov/ecoli/2011/O157_0311/index.html [accessed Jan. 17, 2015].

Anonymous. (2012a). *Investigation Announcement: Multistate Outbreak of E. coli O157:H7 Infections Linked to Romaine Lettuce*. Available at: http://www.cdc.gov/ecoli/2011/ecoliO157/romainelettuce/120711/index.html [accessed Oct. 26, 2012].

Anonymous. (2012b). *Multistate Outbreak of Shiga Toxin-producing Escherichia coli O157:H7 Infections Linked to Organic Spinach and Spring Mix Blend (Final Update)*. Available at: http://www.cdc.gov/ecoli/2012/O157H7-11-12/index.html [accessed Jan. 17, 2015].

Anonymous. (2013). *Multistate Outbreak of Shiga toxin-producing Escherichia coli O157:H7 Infections Linked to Ready-to-Eat Salads (Final Update)*. Available at: http://www.cdc.gov/ecoli/2013/O157H7-11-13/index.html [accessed Jan. 17, 2015].

Anonymous. (2014). *Multistate Outbreak of Shiga toxin-producing Escherichia coli O157:H7 Infections Linked to Ground Beef (Final Update)*. Available at: http://www.cdc.gov/ecoli/2014/O157H7-05-14/index.html [accessed Jan. 17, 2015].

Bao and Wang (2011). Isolation and characterization of bacteriophages of *Salmonella enterica* serovar Pullorum. *Poultry Sci.* 90, 2370-2377. doi: 10.3382/ps.2011-01496

Barrangou et al. (2007). CRISPR provides acquired resistance against viruses in prokaryotes. *Science* 315, 1709-1712. doi: 10.1126/science.1138140

Bartual et al. (2010). Structure of the bacteriophage T4 long tail fiber receptor-binding tip. *Proc. Natl. Acad. Sci. U.S.A.* 107, 20287-20292. doi: 10.1073/pnas.1011218107

Bell et al. (1994). A multistate outbreak of *Escherichia coli* O157:H7-associated bloody diarrhea and hemolytic uremic syndrome from hamburgers: the Washington experience. *JAMA* 272, 1349-1353. doi: 10.1001/jama.1994.03520170059036

Berk et al. (2005). Acid resistance variability among isolates of *Salmonella enterica* serovar Typhimurium DT 104. *J. Appl. Microbiol.* 99, 859-866. doi: 10.1111/j.1365-2672.2005.02658.x Besser et al. (1993). An outbreak of diarrhea and hemolytic uremic syndrome from *Escherichia coli* O157:H7 in fresh-pressed apple cider. *JAMA* 269, 2217-2220. doi: 10.1001/jama.1993.03500170047032

Bickle and Kruger (1993). Biology of DNA restriction. *Microbiol. Rev.* 57, 434-450.

Bilge et al. (1996). Role of the *Escherichia coli* O157:H7 O side chain in adherence and analysis of an rfb locus. *Infect. Immun.* 64, 4795-4801.

Bokete et al. (1997). Genetic and phenotypic analysis of *Escherichia coli* with enteropathogenic characteristics isolated from Seattle children. *J. Infect. Dis.* 175, 1382-1389. doi: 10.1086/516470

Bopp et al. (2003). Detection, isolation, and molecular subtyping of *Escherichia coli* O157:H7 and *Campylobacter jejuni* associated with a large waterborne outbreak. *J. Clin. Microbiol.* 41, 174-180. doi: 10.1128/JCM.41.1.174-180.2003

Bosilevac and Koohmaraie (2011). Prevalence and characterization of non-O157 Shiga toxin-producing *Escherichia coli* isolated from commercial ground beef in the United States. *Appl. Environ. Microbiol.* 77, 2103-2112. doi: 10.1128/AEM.02833-10

Breidt and Caldwell (2011). Survival of *Escherichia coli* O157:H7 in cucumber fermentation brines. *J. Food Sci.* 76, M198-M203. doi: 10.1111/j.1750-3841.2011.02045.x Breidt et al. (2013). "Fermented vegetables," in *Food Microbiology: Fundamentals and Frontiers*, 4th Edn, eds M. P. Doyle and L. R. Beuchat (Washington, D.C.: ASM Press), 841-855.

Calendar (ed.). (1988). *The Bacteriophages*, Vol. 1. New York: Plenum Press.

Carter et al. (2012). Bacteriophage cocktail significantly reduces *Escherichia coli* O157:H7 contamination of lettuce and beef, but does not protect against recontamination. *Bacteriophage* 2, 178-185. doi: 10.4161/bact.22825

Castanie-Cornet et al. (1999). Control of acid resistance in *Escherichia coli*. *J. Bacteriol.* 181, 3525-3535.

Ceyssens et al. (2006). Genomic analysis of *Pseudomonas aeruginosa* phages LKD16 and LKA1: establishment of the ΦKMV subgroup within the T7 supergroup. *J. Bacteriol.* 188, 6924-6931. doi: 10.1128/JB.00831-06

Chang et al. (2005) Isolation and characterization of novel giant *Stenotrophomonas maltophilia* phage ΦSMA5. *Appl. Environ. Microbiol.* 71, 1387-1393. doi: 10.1128/AEM.71.3.1387-1393.2005

Chen and Jiang (2014) Microbiological safety of chicken litter or chicken litter-based organic fertilizers: a review. *Agriculture* 4, 1-29. doi: 10.3390/agriculture4010001

Cheville et al. (1996) rpoS regulation of acid, heat, and salt tolerance in *Escherichia coli* O157:H7. *Appl. Environ. Microbiol.* 62, 1822-1824.

Cleary (1988) Cytotoxin producing *Escherichia coli* and the hemolytic uremic syndrome. *Pediatr. Clin. N. Am.* 35, 458-501.

Cody et al. (1999) An outbreak of *Escherichia coli* O157:H7 infection from unpasteurized commercial apple juice. *Annu. Intern. Med.* 130, 202-209. doi: 10.7326/0003-4819-130-3-199902020-00005

Coffey et al. (2010) Phage and their lysins as biocontrol agents for food safety applications. *Annu. Rev. Food Sci. Technol.* 1, 449-468. doi: 10.1146/annurev-.food.102308.124046

Como-Sebetti et al. (1997) Outbreaks of *Escherichia coli* O157:H7 infection associated with eating alfalfa sprouts—Michigan and Virginia, June-July 1997. *Morb. Mortal. Wkly. Rep.* 46, 741-744.

Diez-Gonzalez and Russell (1999) Factors affecting the extreme acid resistance of *Escherichia coli* O157:H7. *Food Microbiol.* 16, 367-374. doi: 10.1006/fmic.1998.0249

Ellis and Delbruck (1939) The growth of bacteriophage. *J. Gen. Physiol.* 22, 365-384. doi: 10.1085/jgp.22.3.365

Farber and Pagotto (1992) The effect of acid shock on the heat resistance of *Listeria monocytogenes*. *Lett. Appl. Microbiol.* 15, 197-201. doi: 10.1111/j.1472-765X.1992.tb00762.x Ferguson et al. (2013) Lytic bacteriophages reduce *Escherichia coli* O157:H7 on fresh-cut lettuce introduced through cross-contamination. *Bacteriophage* 3:e24323. doi: 10.4161/bact.24323

Foschino et al. (1995) Characterization of two virulent *Lactobacillus fermentum* bacteriophages isolated from sour dough. *J. Appl. Microbiol.* 79, 677-683.

Garcia-Doval and van Raaij (2012) Structure of the receptor-binding carboxyl-terminal domain of bacteriophage T7 tail fibers. *Proc. Natl. Acad. Sci. U.S.A.* 109, 9390-9395. doi: 10.1073/pnas.1119719109

Glass et al. (1992) Fate of *Escherichia coli* O157:H7 as affected by pH or sodium chloride and in fermented, dry sausage. *Appl. Environ. Microbiol.* 58, 2513-2516.

Griffin et al. (1994) "Large outbreak of *Escherichia coli* O157:H7 infections in the western United States: the big picture," in *Recent Advances in Verocytotoxin-Producing Escherichia coli Infections*, eds M. A. Karmali and A. G. Goglio (New York: Elsevier Science Publishing), 7-12.

Griffin and Tauxe (1991) The epidemiology of infections caused by *Escherichia coli* O157:H7, other enterohemorrhagic *E. coli* and the associated hemolytic uremic syndrome. *Epidemiol. Rev.* 13, 60-98.

Guenther et al. (2009) Virulent bacteriophage for efficient biocontrol of *Listeria monocytogenes* in ready-to-eat foods. *Appl. Environ. Microbiol.* 75, 93-100. doi: 10.1128/AEM.01711-08

Gyles (2007) Shiga toxin-producing *Escherichia coli*: an overview. *J. Anim Sci.* 85(E. Suppl.), E45E62.

Hagens and Loessner (2010) Bacteriophage for biocontrol of foodborne pathogens: calculations and considerations. *Curr. Pharm. Biotechnol.* 11, 58-68. doi: 10.2174/138920110790725429

Hashemolhosseini et al. (1994) Alterations of receptor specificities of coliphages of the T2 family. *J. Mol. Biol.* 240, 105-110. doi: 10.1006/jmbi.1994.1424

Hilborn et al. (2000) An outbreak of *Escherichia coli* O157:H7 infections and haemolytic uraemic syndrome associated with consumption of unpasteurized apple cider. *Epidemiol. Infect.* 124, 31-36. doi: 10.1017/S0950268899003258

Hill (1993) Bacteriophage and bacteriophage resistance in lactic acid bacteria. *FEMS Microbiol. Rev.* 12, 87-108. doi: 10.1111/j.1574-6976.1993.tb00013.x Jinneman et al. (2003) Multiplex real-time PCR method to identify shiga toxins, stx1 and stx2 and *E. coli* O157:H7 Serogroup. *Appl. Environ. Microbiol.* 69, 6327-6333. doi: 10.1128/AEM.69.10.6327-6333.2003

Jordan et al. (1999) Survival of low-pH stress by *Escherichia coli* O157:H7: correlation between alterations in the cell envelope and increased acid tolerance. *Appl. Environ. Microbiol.* 65, 3048-3055.

Karmali (1989) Infection by verotoxin-producing Escherichia coll. *Clin. Microbiol. Rev.* 2, 15-38.

Kudva et al. (1999) Biocontrol of *Escherichia coli* O157 with O157-specific bacteriophages. *Appl. Environ. Microbiol.* 65, 3767-3773.

Large et al. (2005) Variation in acid resistance among shiga toxin-producing clones of pathogenic *Escherichia coli*. *Appl. Environ. Microbiol.* 71, 2493-2500. doi: 10.1128/AEM.71.5.2493-2500.2005

Leiman et al. (2004) Three-dimensional rearrangement of proteins in the tail of bacteriophage T4 on infection of its host. *Cell* 118, 419-429. doi: 10.1016/j.cel1.2004.07.022

Leuschner et al. (1993) Characterization of a virulent *Lactobacillus* sake phage PWH2. *Appl. Microbiol. Biotechnol.* 39, 617-621. doi: 10.1007/BF00205063

Leyer and Johnson (1993) Acid adaptation induces cross-protection against environmental stress in *Salmonella typhimurium*. *Appl. Environ. Microbiol.* 59, 1842-1847.

Leyer et al. (1995). Acid adaptation of *Escherichia coli* O157:H7 increases survival in acidic foods. *Appl. Environ. Microbiol.* 61, 3752-3755.

Lin et al. (1996) Mechanisms of acid resistance in enterohemorrhagic *Escherichia coli*. *Appl. Environ. Microbiol.* 62, 3094-3100.

Lu et al. (2005). Sequence analysis of the *Lactobacillus plantarum* bacteriophage JL-1. *Gene* 348, 45-54. doi: 10.1016/j.gene.2004.12.052

Lu et al. (2003) Isolation and characterization of a Lactobacillus plantarum bacteriophage JL-1 from a cucumber fermentation. *Int. J. Food Microbiol.* 84, 225-235. doi: 10.1016/S0168-1605(03)00111-9

Mahony et al. (2011) Bacteriophages as biocontrol agents of food pathogens. *Curr. Opin. Biotechnol.* 22, 157-163. doi: 10.1016/j.copbio.2010.10.008

Mead and Griffin (1998) *Escherichia coli* O157:H7. *Lancet* 352, 1207-1212. doi: 10.1016/S0140-6736(98)01267-7

Mead et al. (1999) Food-related illness and death in the United States. *Emerg. Infect. Dis.* 5, 607-625. doi: 10.3201/eid0505.990502

Mizoguchi et al. (2003) Coevolution of bacteriophage PP01 and *Escherichia coli* O157:H7 in continuous culture. *Appl. Environ. Microbiol.* 69, 170-176. doi: 10.1128/AEM.69.1.170-176.2003

Morita et al. (2002) Characterization of a virulent bacteriophage specific for *Escherichia coli* O157:H7 and analysis of its cellular receptor and two tail fiber genes. *FEMS Microbiol. Lett.* 211, 77-83. doi: 10.1111/j.1574-6968.2002.tb11206.x Nataro and Kaper (1998) Diarrheagenic *Escherichia coli*. *Clin. Microbiol. Rev.* 11, 142-201.

Nechaev and Severinov (2008) The elusive object of desire—interactions of bacteriophages and their hosts. *Curr. Opin. Microbiol.* 11, 186-193. doi: 10.1016/j.mib.2008.02.009

O'Flaherty et al. (2009) Bacteriophage and their lysins for elimination of infectious bacteria. *FEMS Microbiol. Rev.* 33, 801-819. doi: 10.1111/j.1574-6976.2009.00176.x O'Flynn et al. (2004) Evaluation of a cocktail of three bacteriophages for biocontrol of *Escherichia coli* O157:H7. *Appl. Environ. Microbiol.* 70, 3417-3424. doi: 10.1128/AEM.70.6.3417-3424.2004

Ongeng et al. (2013) Fate of *Escherichia coli* O157:H7 and *Salmonella enterica* in the manure-amended soil-plant ecosystem of fresh vegetable crops: a review. *Crit. Rev. Microbiol.* doi: 10.3109/1040841X.2013.829415 [Epub ahead of print].

Park et al. (2012) Characterization and comparative genomic analysis of a novel bacteriophage, SFP10, simultaneously inhibiting both *Salmonella enterica* and *Escherichia coli* O157:H7. *Appl. Environ. Microbiol.* 78, 58-69. doi: 10.1128/AEM.06231-11

Price et al. (2000) Role of rpoS in acid resistance and fecal shedding of *Escherichia coli* O157:H7. *Appl. Environ. Microbiol.* 66, 632-637. doi: 10.1128/AEM.66.2.632-637.2000

Price et al. (2004) Acid resistance systems required for survival of *Escherichia coli* O157:H7 in the bovine gastrointestinal tract and in apple cider are different. *Appl. Environ. Microbiol.* 70, 4792-4799. doi: 10.1128/AEM.70.8.4792-4799.2004

Rangel et al. (2005) Epidemiology of *Escherichia coli* O157:H7 outbreaks, United States, 1982-2002. *Emerg. Infect. Dis.* 11, 603-609. doi: 10.3201/eid1104.040739

Raya et al. (2006) Isolation and characterization of a new T-even bacteriophage, CEV1, and determination of its potential to reduce *Escherichia coli* O157:H7 levels in sheep. *Appl. Environ. Microbiol.* 72, 6405-6410. doi: 10.1128/AEM.03011-05

Remis et al. (1984) Sporadic cases of hemorrhagic colitis associated with *Escherichia coli* O157:H7. *Annu. Intern. Med.* 101, 728-742. doi: 10.7326/0003-4819-101-5-624

Riede (1987). Receptor specificity of the short tail fibres (gp12) of T-even type *Escherichia coli* phages. *Mol. Gen. Genet.* 206, 110-115. doi: 10.1007/BF00326544

Riley, et al. (1983) Hemorrhagic colitis associated with a rare *Escherichia coli* serotype O157:H7. *N. Engl. J. Med.* 308, 681-685. doi: 10.1056/NEJM198303243081203

Santos et al. (2011) Genomic and proteomic characterization of the broad-host-range *Salmonella* phage PVP-SE1: creation of a new phage genus. *J. Virol.* 85, 11265-11273. doi: 10.1128/JV1.01769-10

Shahrbabak et al. (2013) Isolation, characterization and complete genome sequence of PhaxI: a phage of *Escherichia coli* O157: H7. *Microbiology* 159, 1629-1638. doi: 10.1099/mic.0.063776-0

Sharma (2013) Lytic bacteriophages: potential interventions against enteric bacterial pathogens on produce. *Bacteriophage* 3, e25518. doi: 10.4161/bact.25518

Sharma et al. (2009). Effectiveness of bacteriophages in reducing *Escherichia coli* O157:H7 on fresh-cut cantaloupes and lettuces. *J. Food Protien* 72, 1481-1485.

Sheng et al. (2006). Application of bacteriophages to control intestinal *Escherichia coli* O157:H7 levels in ruminants. *Appl. Environ. Microbiol.* 72, 5359-5366. doi: 10.1128/AEM.00099-06

Sheng et al. (2008). Characterization of an *Escherichia coli* O157:H7 O-antigen deletion mutant and effect of the deletion on bacterial persistence in the mouse intestine and colonization at the bovine terminal rectal mucosa. *Appl. Environ. Microbiol.* 74, 5015-5022. doi: 10.1128/AEM.00743-08

Swerdlow et al. (1992) A waterborne outbreak in Missouri of *Escherichia coli* O157:H7 associated with bloody diarrhea and death. *Annu. Intern. Med.* 117, 812-819. doi: 10.7326/0003-4819-117-10-812

Tanji et al. (2004) Toward rational control of *Escherichia coli* O157:H7 by a phage cocktail. *Appl. Microbiol. Biotechnol.* 64, 270-274. doi: 10.1007/s00253-003-1438-9

Tarr (1995) *Escherichia coli* O157:H7: clinical, diagnostic, and epidemiological aspects of human infection. *Clin. Infect. Dis.* 20, 1-10. doi: 10.1093/clinids/20.1.1

Tomat et al. (2013) Phage biocontrol of enteropathogenic and shiga toxin-producing *Escherichia coli* in meat products. *Front. Cell. Infect. Microbiol.* 3:20. doi: 10.3389/fcimb.2013.00020

Topley and Wilson (1990) *Principles of Bacteriology, Virology and Immunity.* London: B. C. Decker Publisher.

Tuttle et al. (1999) Lessons from a large outbreak of *Escherichia coli* O157:H7 infections: insights into the infectious dose and method of widespread contamination of hamburger patties. *Epidemiol. Infect.* 122, 185-192. doi: 10.1017/S0950268898001976

Vasu and Nagaraja (2013) Diverse functions of restriction-modification systems in addition to cellular defense. *Microbiol. Mol. Biol. Rev.* 77, 53-72. doi: 10.1128/MMBR.00044-12

Viazis et al. (2011) Reduction of *Escherichia coli* O157:H7 viability on leafy green vegetables by treatment with a bacteriophage mixture and trans-cinnamaldehyde. *Food Microbiol.* 28, 149-157. doi: 10.1016/j.fm.2010.09.009

Weagant et al. (1994) Survival of *Escherichia coli* O157:H7 in mayonnaise and mayonnaise-based sauces at room and refrigerated temperatures. *J. Food Protein* 57, 629-631.

Yu et al. (2000) Characterization of the distal tail fiber locus and determination of the receptor for phage AR1, which specifically infects *Escherichia coli* O157:H7. *J. Bacteriol.* 182, 5962-5968. doi: 10.1128/J 6.182.21.5962-5968.2000.

What is claimed is:

1. A method for the prevention of foodborne illness caused by *Escherichia coli* (*E. coli*) O157:H7 strains comprising, preparing a food item by contacting the food item with isolated phage Φ241 in an amount effective to lyse at least 99.9% of the E. coli O157:H7 present in the food item while leaving E. coli strains other than O157:H7 unaffected, wherein the phage Φ241 is isolated from an environment having a salinity of 5% and a pH of 3.7.

2. The method of claim 1 where the contacting is at least one hour.

3. The method of claim 1 where the lysis continues for several hours.

4. The method of claim 1 where an initial multiplicity of infection is 10, 3, or 0.3.

5. The method of claim 1 where the final phage concentration in the food item may reach $5'10^8$ PFU/ml.

6. The method of claim 1 further comprising an initial multiplicity of infection of 10 for the bacteriophage Φ241 and a contact time of about two hours.

7. The method of claim 1 where the food item is a vegetable, a fruit, a meat, a dairy product, or a juice.

8. The method of claim 1 where the food item is a food-contact surface.

9. The method of claim 8 where the food-contact surface is at least one of a utensil, table top, cutting board, food processing equipment, or packaging material.

10. The method of claim 1 where the contacting is by direct addition or by spraying on the food item.

11. The method of claim 1 where the bacteriophage Φ241 is in a liquid.

12. A method for preparing a food item, the method comprising contacting the food item with an isolated bacteriophage Φ241 at an initial multiplicity of infection of 10 for a time of about 2 hours at 37° C., wherein the bacteriophage is isolated from an environment having a salinity of 5% and wherein 99.9% of *Escherichia coli* (*E. coli*) O157:H7 present in the food item is lysed.

13. A method for detecting the presence of *Escherichia coli* (*E. coli*) O157:H7 in a high salinity environment, the method comprising contacting a bacteriophage Φ241 with an item suspected of having *E. coli* O157:H7 in the high salinity environment having a salinity of between 2.3% and 5.0% of salt (weight by volume), and detecting the presence of an *E.coli* O157:H7 lysis product.

14. The method of claim 13 where the item is a food item.

15. The method of claim 14 where contacting is by direct addition of the bacteriophage Φ241 into or onto the food item.

16. The method of claim 13 where the lysis product is a *E. coli* O157:H7 nucleic acid or a *E. coli* O157:H7 intracellular protein, or fragment thereof.

17. The method of claim 16 where the *E. coli* O157:H7 nucleic acid is DNA or RNA.

18. The method of claim 16 where the lysis product is a *E. coli* O157:H7 intracellular protein and is an enzyme, the method further comprises adding a substrate of the enzyme and the detection comprises detecting a product of the enzyme.

* * * * *